United States Patent
Wang et al.

(10) Patent No.: US 10,519,509 B2
(45) Date of Patent: Dec. 31, 2019

(54) METHODS AND COMPOSITIONS FOR THE DETECTION OF CALR MUTATIONS IN MYELOPROLIFERATIVE DISEASES

(71) Applicant: QUEST DIAGNOSTICS INVESTMENTS INCORPORATED, Wilmington, DE (US)

(72) Inventors: Yongbao Wang, San Juan Captistrano, CA (US); Daniel Jones, San Juan Captistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 144 days.

(21) Appl. No.: 15/135,957

(22) Filed: Apr. 22, 2016

(65) Prior Publication Data

US 2016/0312303 A1   Oct. 27, 2016

Related U.S. Application Data

(60) Provisional application No. 62/151,742, filed on Apr. 23, 2015.

(51) Int. Cl.
   *C12Q 1/68* (2018.01)
   *C12P 19/34* (2006.01)
   *C12Q 1/6886* (2018.01)

(52) U.S. Cl.
   CPC ...... *C12Q 1/6886* (2013.01); *C12Q 2600/118* (2013.01); *C12Q 2600/156* (2013.01)

(58) Field of Classification Search
   CPC ............ C12Q 1/6886; C12Q 2600/118; C12Q 2600/156
   See application file for complete search history.

(56) References Cited

U.S. PATENT DOCUMENTS

| | | |
|---|---|---|
| 7,781,199 B2 | 8/2010 | Vainchenker et al. |
| 8,841,074 B2 | 9/2014 | Ma et al. |
| 2015/0079091 A1 | 3/2015 | Kralovics et al. |

FOREIGN PATENT DOCUMENTS

EP   2 808 338 A1   12/2014

OTHER PUBLICATIONS ss994105863—Submitted SNP(ss) Report in Submission Format (Apr. 23, 2014) from www.ncbi.nlm.nih.gov, 1 page.*
GenBank Locus NM_004343 "*Homo sapiens* calreticulin (CALR), mRNA" (Apr. 6, 2014), from www.ncbi.nlm.nih.gov, 7 pages.*
Hsu et al, BioTechniques 25:692-696 (Oct. 1998).*
Lundberg P. et al, Blood, Apr. 3, 2014, vol. 123, No. 14., p. 2220-2228.*
Bejanyan N. et al.Cancer 2012;118:3968-76.*
Zamora L. et al. Co-existence of JAK2 V617F and CALR mutations in primary myelofibrosis, Accepted author version posted online: Feb. 17, 2015, Leukemia & Lymphoma, 56:10, 2973-2974 (Year: 2015).*
Bench A.J. et al. Molecular diagnosis of the myeloproliferative neoplasms: UK guidelines for the detection of JAK2 V617F and other relevant mutations. British Journal of Haematology, 2013, 160, 25-34 (Year: 2013).*
Gotlib, "Muttion of the Calreticulin (CALR) Gene in Myeloproliferative Neoplasms," The Hematologist, vol. 12, Issue 1, Jan. 2015.
Rumi et al., "Clinical effect of driver mutations of JAK2, CALR, or MPL in primary myelofibrosis," Blood, vol. 124, No. 7, pp. 1062-1069, Aug. 2014.
Assaf et al., Analysis of phenotype and outcome in essential thrombocythemia with CALR or JAK2 mutations, Haematologica, vol. 100, No. 7, pp. 893-897, 2015.
Lim et al., "Frequent CALR exon 9 alterations in JAK2 V617F-mutated essential thrombocythemia detected by high-resolution melting analysis," Blood Cancer Journal, vol. 5, e295, Mar. 2015.
Wang et al., In-Frame Exon 9 CALR Indels Co-Occur with Other Alterations in the JAK-STAT Pathway in Myeloproliferative Neoplasms, ASH Annual Meeting, San Francisco, CA, Dec. 6-9, 2014, Poster 4588.
Klampfl et al., "Somatic Mutations of Calreticulin in Myeloproliferative Neoplams," The New England Journal of Medicine, vol. 369, No. 25, pp. 2379-2390, Dec. 2013.
Wang et al., "In-Frame Exon 9 CALR Deletions Co-Occur with Other Alterations in the JAK-STAT Pathway in Myeloproliferative Neoplasms," 56th ASH Annual Meeting and Exposition, Session 635, Abstract 4588, Dec. 6-9, 2014.
Lim et al., "Frequent CALR exon 9 alterations in JAK2 V617F-mutated essential thrombocythemia detected by high-resolution melting analysis," Blood Cancer Journal, vol. 5, No. e295, Mar. 20, 2015.
GenBank Entry NM_004343 "*Homo sapiens* calreticulin (CALR), mRNA," May 11, 2014.
International Search Report dated Oct. 26, 2016 in application No. PCT/US2016/28877.
Labastida-Mercado et al., "The mutation profile of JAK2, MPL and CALR in Mexican patients with Philadelphia chromosome-negative myeloproliferative neoplasms," Hematol. Oncol. Stem Cell Ther., Mar. 1, 2015, 8(1):16-21.
Mughal et al., "Novel Insights Into the Biology and Treatment of Chronic Myeloproliferative Neoplasms," Leukemia and Lymphoma, Nov. 19, 2014, 56(7):1938-1948.
Rumi et al., "Clinical effect of driver mutations of JAK2, CALR, or MPL in primary myelofibrosis," Blood, Jul. 1, 2014, 124(7):1062-1069.
Supplementary European Search Report dated Oct. 17, 2018, in EP 16783950.5.

(Continued)

*Primary Examiner* — Stephen T Kapushoc
(74) *Attorney, Agent, or Firm* — Foley & Lardner LLP

(57) ABSTRACT

Provided herein are methods and compositions for the detection of in-frame deletion germline mutations in the CALR gene. Also provided are methods for determining the prognosis of myeloproliferative diseases and the likelihood of developing somatic mutations in genes involved in the JAK-STAT pathway.

14 Claims, 5 Drawing Sheets

Specification includes a Sequence Listing.

(56) References Cited

OTHER PUBLICATIONS

Xu et al., "A report on the co-occurrence of JAK2V617F and CALR mutations in myeloproliferative neoplasm patients," Ann. Hematol., Nov. 5, 2014, 94(5):865-867.

* cited by examiner

A p.D397_D400>D

B

| | | | |
|---|---|---|---|
| *H. sapiens* | 381 | EAEDKEDDEDKDEDEE<u>DEED</u>KEEDEEED-V | 409 |
| *P. troglodytes* | 381 | EAEDKEDDEDKD---E<u>DEED</u>KEEDEEED-V | 406 |
| *M. mulatta* | 381 | EAEDKEDDEDKDEDEE<u>DEED</u>KEEDEEED-V | 409 |
| *C. lupus* | 381 | EA-DKEDEEDKDEDEE<u>DEDD</u>KEEEEEDDAA | 409 |
| *M. musculus* | 381 | EAEDKEDDDDRDEDEDEEDEKEEDEEE--S | 408 |
| *R. norvegicus* | 381 | EAEDKEDEDDRDEDEDEEDEKEEDEED--A | 408 |

# METHODS AND COMPOSITIONS FOR THE DETECTION OF CALR MUTATIONS IN MYELOPROLIFERATIVE DISEASES

BACKGROUND OF THE INVENTION

This application claims priority to U.S. Provisional Application No. 62/151,742, filed Apr. 23, 2015, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 23, 2016, is named 034827-0839_SL.txt and is 35,092 bytes in size.

BACKGROUND OF THE INVENTION

Chronic myeloproliferative neoplasms (MPNs) are clonal hematopoietic stem cell malignancies characterized by excessive production of blood cells. Polycythemia vera (PV), essential thrombocythemia (ET), and idiopathic myelofibrosis (MF) are the three most common BCR/ABL1-negative MPNs and are associated with thrombosis and hemorrhage, splenomegaly, and the risk of transformation to acute myeloid leukemia.

The classification of myeloproliferative neoplasms (MPN) has focused on specific disease-defining, mutually exclusive translocations and mutations in key growth regulatory genes. Some of these genetic alterations are tightly associated with prior clinically-defined entities, such as BCR-ABL1 rearrangement in chronic myeloid leukemia (CIVIL) and JAK2 exon 12 mutations in polycythemia vera (PV). Other mutations, such as JAK2 V617F, myeloproliferative leukemia gene (MPL) mutations and colony-stimulating factor 3 receptor (CSF3R) mutations, have also been found to be associated with MPN (Cazzola et al. *Blood* 2014 Jun. 12; 123(24):3714-9).

Somatic mutations in the chaperone gene calreticulin (CALR) have been identified in essential thrombocythemia (ET) and primary myelofibrosis (PMF), and are essentially mutually exclusive with JAK2 and MPL mutations (Klampfl et al. *N. Eng J Med* 2013 Dec. 19; 369(25):2379-90; Lundberg et al. *Blood* 2014 Apr. 3; 123(14):2220-8; Nangalia et al. *N Engl J Med* 2013 Dec. 19; 369(25):2391-405; Tefferi et al. *Leukemia* 2014 July; 28(7):1568-70; Vannucchi et al. *Leukemia* 2014 September; 28(9):1811-8). These CALR mutations are localized to exon 9 of the CALR gene and are largely specific for ET and PMF, being found only rarely in cases of myelodysplasia. Normal and mutant CALR proteins can differentially affect the subcellular trafficking of JAK-STAT signaling components (Rampal et al. *Blood* 2014 May 29; 123(22):e123-e133). The two most common disease-associated CALR mutations in ET and PMF are a 52-base pair (bp) deletion at codon 367 (type 1) and a 5-bp TTGTC insertion at codon 385 (type 2). Both produce a +1 bp frameshift that generates novel C-terminal protein sequences with a shift from acidic to basic amino acid residues, which is believed to affect chaperone activity (Rizvi et al. *Mol Cell* 2004 Sep. 24; 15(6):913-23). Other +1 bp frameshift mutations (types 3-30) and 3 in-frame exon 9 deletions (Ensembl TMP_ESP_19_13054649 E393_E395del3, and TMP_ESP_19_13054685 and COSM3355757 (p.E405_408) have also been described (Klampfl et al. *N Engl J Med* 2013 Dec. 19; 369(25):2379-90).

SUMMARY OF THE INVENTION

Provided herein, in certain embodiments, are methods for detecting in-frame deletion mutations (indel) in exon 9 of the CALR gene. In some embodiments, the mutation is selected from among p.E381_A382>A deletion, a p.D397_D400>D deletion, and a p.E405_V409>V deletion. The methods of detecting can be employed, for example, for the diagnosis of a myeloproliferative disease, determining the likelihood of developing a myeloproliferative disease, determining the prognosis of a myeloproliferative disease, monitoring a myeloproliferative disease, selecting a subject for treatment of a myeloproliferative disease and/or determining the likelihood of having or developing a mutation in an additional gene associated with a myeloproliferative disease. In some embodiments, the methods further comprise detection of one or more additional mutations associated with a myeloproliferative disease.

Provided herein, in certain embodiments, are methods for detecting an in-frame deletion mutation (Indel) in exon 9 of the calreticulin (CALR) gene comprising: performing a nucleic acid detection assay on a patient sample to detect an CALR exon 9 Indel mutation, wherein the mutation is selected from the group consisting of p.E381_A382>A, p.D397_D400>D, p.E405_V409>V. In some embodiments, the in-frame deletion mutation corresponds to a genomic deletion selected from among chr19:g.13054615_13054617, chr19:g.13054664_13054672, and chr19:g.13054687_13054698.

Provided herein, in certain embodiments, are methods for detecting an in-frame deletion mutation (Indel) in exon 9 of the calreticulin (CALR) gene in a subject, where the subject is suspected of having a CALR-related disease or a JAK2-related disease or condition. In some embodiments, the CALR-related or JAK2-related disease or condition is a myeloproliferative disease. In some embodiments, the myeloproliferative disease is selected from among polycythemia vera, essential thrombocythemia, idiopathic myelofibrosis, and unclassified myeloproliferative disease. In some embodiments, the mutation is selected from the group consisting of p.E381_A382>A, p.D397_D400>D, p.E405_V409>V. In some embodiments, the in-frame deletion mutation corresponds to a genomic deletion selected from among chr19:g.13054615_13054617, chr19:g.13054664_13054672, and chr19:g.13054687_13054698.

Provided herein, in certain embodiments, are methods for detecting an in-frame deletion mutation (Indel) in exon 9 of the calreticulin (CALR) gene in a subject, where the subject has received one or more treatments for a CALR-related disease or condition or a JAK2-related disease or condition. In some embodiments, the CALR-related or JAK2-related disease or condition is a myeloproliferative disease. In some embodiments, the disease or condition is selected from among polycythemia vera, essential thrombocythemia, idiopathic myelofibrosis, and unclassified myeloproliferative disease myeloproliferative disease. In some embodiments, the one or more treatments comprise phlebotomy, platelet apheresis, transfusion therapy, chemotherapy, radiation therapy, surgery, biologic therapy, targeted therapy, high-dose, or stem cell transplant. In some embodiments, the mutation is selected from the group consisting of p.E381_A382>A, p.D397_D400>D, p.E405_V409>V. In some embodiments, the in-frame deletion mutation corresponds to a genomic deletion selected from among chr19: g.13054615_13054617, chr19:g.13054664_13054672, and chr19:g.13054687_13054698.

Provided herein, in certain embodiments, are methods for diagnosing a hematopoietic disease in a patient comprising: performing a nucleic acid detection assay on a sample comprising CALR nucleic acid from a patient to determine whether the nucleic acid comprises a CALR exon 9 Indel mutation, wherein the mutation is selected from the group consisting of p.E381_A382>A, p.D397_D400>D, p.E405_V409>V; and diagnosing the patient as having a hematopoietic disease when the CALR exon 9 Indel mutation is detected. In some embodiments, the in-frame deletion mutation corresponds to a genomic deletion selected from among chr19:g.13054615_13054617, chr19: g.13054664_13054672, and chr19:g.13054687_13054698. In some embodiments, the methods further comprise treating the patient if the CALR mutation exon 9 Indel mutation is present. In some embodiments, the hematopoietic disease is a myeloproliferative disease. In some embodiments, the myeloproliferative disease is polycythemia vera, essential thrombocythemia, idiopathic myelofibrosis, and unclassified myeloproliferative disease In some embodiments, the methods of detecting a CALR exon 9 Indel mutation comprise nucleic acid amplification, for example, using a primer pair, comprising a forward primer and a reverse primer that flank the deletion mutation. In some embodiments, the nucleic acid amplification method comprises polymerase chain reaction (PCR), reverse transcription polymerase chain reaction (RT-PCR), real-time PCR (qPCR), or nested PCR. In some embodiments, the method comprises reverse transcription of RNA into cDNA. In some embodiments, the method comprises using a labeled oligonucleotide probe. In some embodiments, the labeled probe hybridizes to a nucleic acid having the deletion, and does not hybridize to a wild type sequence. In some embodiments, the labeled probe comprises from about 10 to 30 consecutive nucleotides of the sequence SEQ ID NO: 1 and comprises the CALR exon 9 deletion site. In some embodiments, the method comprises sequencing an amplicon comprising all or a portion of CALR exon 9 comprising the deletion. In some embodiments, the method comprises detecting an amplicon comprising all or a portion of CALR exon 9 comprising the deletion by electrophoresis. In some embodiments, the amplicon is detected using a labeled oligonucleotide probe. In some embodiments, the nucleic acid is isolated from the sample prior to detecting. Exemplary probes or primers for detection include nucleic acid molecules having the sequence of any of SEQ ID NO: 10, 11, 12, and 13. In some embodiments, the method comprises amplification of a portion of CALR exon 9 comprising the deletion using a one or more primer pairs. In some embodiments, primer pair comprises a forward primer selected from among SEQ ID NO:10 or 12. In some embodiments the, primer pair comprises a reverse primer selected from among SEQ ID NO:11 or 13. In some embodiments, primer pair comprises a forward primer selected from among SEQ ID NO:10 or 12 and a reverse primer selected from among SEQ ID NO:11 or 13.

In some embodiments, the CALR exon 9 mutation is detected in a nucleic acid sample containing DNA or RNA. In some embodiments, the nucleic acid is genomic DNA. In some embodiments, the nucleic acid is cDNA. In some embodiments, the nucleic acid is from a biological sample obtained from a patient. In some embodiments, the patient sample is a fluid sample or a tissue sample. In some embodiments, the patient sample is a blood, serum, or plasma sample. In some embodiments, the patient sample is a biopsy sample. In some embodiments, the methods further comprise obtaining the patient sample from the patient. In some embodiments, the patient has a myeloproliferative disease. In some embodiments, the myeloproliferative disease is selected from among polycythemia vera, essential thrombocythemia, idiopathic myelofibrosis, and unclassified myeloproliferative disease.

In some embodiments, the methods further comprise detecting one or more additional mutations in one or more additional genes associated with a myeloproliferative disease. In some embodiments, the one or more additional genes is a JAK-STAT pathway gene. In some embodiments, the one or more additional genes is JAK2, MPL, CSFR3R, ASXL1, or ZRSR2. In some embodiments, the one or more additional mutations is a single nucleotide polymorphism, insertion, deletion, duplication or translocation. In some embodiments, the one or more additional mutations is selected from among a mutation in exon 12 of JAK2, in exon 14 of JAK2, exon 10 of MPL or exon 14 or exon 17 CSFR3R. In some embodiments, the one or more additional mutations is selected from among JAK2 V617F, MPL W515L, CSFR3R A470T, ASXL1 D954fs*26, or ZRSR2 S449_R450du. In some embodiments, JAK2 V617F is detected. In some embodiments, the additional mutation is a mutation in JAK2 as disclosed in Table 2 of U.S. Pat. No. 8,512,948.

In some embodiments, detecting a mutation provided herein further comprises analyzing using an analytical device. In some embodiments, the analytical device comprises a computer. In some embodiments, the analytical device comprises a sequence analyzer.

In some embodiments the methods further comprise administering a therapy to the patient if the patient has a CALR exon 9 mutation provided herein. In some embodiments the therapy comprises phlebotomy, platelet apheresis, transfusion therapy, chemotherapy, radiation therapy, surgery, biologic therapy, targeted therapy, high-dose, or stem cell transplant. In some embodiments the therapy comprises administration of arsenic trioxide, azacitidine, cyclophosphamide, cytarabine, dasatinib, daunorubicin hydrochloride, decitabine, doxorubicin hydrochloride, imatinib mesylate, nilotinib, ruxolitinib phosphate, and vincristine sulfate.

Provided herein, in certain embodiments, are methods for determining the likelihood that a patient will develop a mutation in a JAK-STAT pathway gene, comprising: performing a nucleic acid detection assay on a sample comprising CALR nucleic acid from a patient to determine whether the nucleic acid comprises a CALR exon 9 Indel mutation, wherein the mutation is selected from the group consisting of p.E381_A382>A, p.D397_D400>D, p.E405_V409>V; and diagnosing said individual as having an increased likelihood of developing a mutation in a JAK-STAT pathway gene if the CALR exon 9 Indel mutation is detected. In some embodiments the JAK-STAT pathway gene is JAK2, MPL, CSFR3R, ASXL1, or ZRSR2. In some embodiments the mutation is selected from among a mutation in exon 12 of JAK2, exon 14 of JAK2, exon 10 of MPL or exon 14 or exon 17 of CSFR3R. In some embodiments the one or more additional mutations is selected from among JAK2 V617F, MPL W515L, CSFR3R A470T, ASXL1 D954fs*26, or ZRSR2 S449_R450du. In some embodiments the patient has a myeloproliferative disease. In some embodiments the myeloproliferative disease is selected from among polycythemia vera, essential thrombocythemia, idiopathic myelofibrosis, and unclassified myeloproliferative disease. In some embodiments, the methods further comprise performing a nucleic acid detection assay on a sample to detect a mutation in a JAK-STAT pathway gene. In some embodiments, the JAK-STAT pathway gene is JAK2, MPL, CSFR3R, ASXL1, or ZRSR2.

Provided herein, in certain embodiments, are methods for determining the prognosis of a patient having a myeloproliferative disease, comprising: performing a nucleic acid detection assay on a sample comprising CALR nucleic acid from a patient to determine whether the nucleic acid comprises a CALR exon 9 Indel mutation, wherein the mutation is selected from the group consisting of p.E381_A382>A, p.D397_D400>D, p.E405_V409>V; and diagnosing the patient as having a poor prognosis when the CALR exon 9 Indel mutation is detected. In some embodiments, the myeloproliferative disease is selected from among polycythemia vera, essential thrombocythemia, idiopathic myelofibrosis, and unclassified myeloproliferative disease.

Provided herein, in certain embodiments, are kits comprising a primer or probe that is complementary to and specifically hybridizes to a target nucleic acid comprising a CALR exon 9 Indel mutation in a nucleic acid sample, wherein the mutation is selected from the group consisting of p.E381_A382>A, p.D397_D400>D, p.E405_V409>V. In some embodiments, the kit further comprises enzymes suitable for amplifying a CALR nucleic acid. In some embodiments, the primer or probe comprises from about 10 to 30 consecutive nucleotides of the sequence SEQ ID NO: 1 and comprises the CALR exon 9 deletion site (e.g. spans the breakpoint site of the deletion). In some embodiments, the primer or probe contains about at least one nucleotide on both sides of the deletion breakpoint). In some embodiments, the primer or probe is labeled with one or more of a radioisotope, a fluorophore, a chromophore, a dye, an enzyme, or time of flight (TOF) carrier. In some embodiments, the primer or probe is configured to indicate hybridization or binding by polymerase chain reaction (PCR), reverse transcription PCR (RT-PCR), fluorescence resonance energy transfer (FRET), chemiluminescence, enzymatic signal amplification, electron dense particles, magnetic particles, capacitance coupling or mass spectrometry. In some embodiments, the probe is fixed to a substrate in a form of a microarray. In some embodiments, the kit further comprises a control primer or probe indicative of a reference CALR sequence.

Provided herein, in certain embodiments, are isolated CALR proteins, comprising an exon 9 in-frame amino acid deletion mutation selected from the group consisting of p.E381_A382>A, p.D397_D400>D, p.E405_V409>V.

Provided herein, in certain embodiments, are isolated nucleic acid molecules having a nucleotide sequence encoding a CALR protein, comprising an exon 9 in-frame amino acid deletion mutation selected from the group consisting of p.E381_A382>A, p.D397_D400>D, p.E405_V409>V. In some embodiments, the isolated nucleic acid molecule is operably linked to a promoter. Provided herein, in certain embodiments, are cloning or expression vectors comprising any of the isolated nucleic acid molecules provided herein. In some embodiments, the vector is a viral vector or a plasmid vector.

Provided herein, in certain embodiments, are cells, for example, mammalian cells comprising any of the isolated nucleic acid molecules or vectors provided herein.

Provided herein, in certain embodiments, are non-human transgenic animals that comprise any of the isolated nucleic acid molecules or vectors provided herein.

Provided herein, in certain embodiments, are oligonucleotide probes or primers comprising from about 10 to 30 consecutive nucleotides of the sequence SEQ ID NO: 1 and comprising the CALR exon 9 deletion site. Exemplary probes or primers include nucleic acid molecules having the sequence of any of SEQ ID NOS: 10, 11, 12, and 13.

In some embodiments, an additional variant for detection in addition to the CALR exon 9 indel mutations provided herein is selected from a variant in a gene selected from among ASXL1, CALR, CBL, CEBPA, CSF3R, DDX41, DNMT3A, EZH2, FLT3, GATA1, IDH1, IDH2, JAK2, KDM6A, KIT, KRAS, MLL, MPL, NPM1, NRAS, PTPN11, RUNX1, SETBP1, SF3B1, SRSF2, TET2, TP53, U2AF1, WT1 and ZRSR2.

In some embodiments, the additional variant for detection in addition to the CALR exon 9 indel mutations provided herein is selected from a variant in a gene selected from among ABL1, ASXL1, ATRX, BCOR, BCORL1, BRAF, CALR, CBL, CBLB, CBLC, CDKN2A, CEBPA, CSF3R, CUX1, DDX41, DNMT3A, ETV6/TEL, EZH2, FBXW7, FLT3, GATA1, GATA2, GNAS, HRAS, IDH1, IDH2, IKZF1, JAK2, JAK3, KDM6A, KIT, KRAS, MLL, MPL, MYD88, NOTCH1, NPM1, NRAS, PDGFRA, PHF6, PTPN11, RAF21, RUNX1, SETBP1, SF3B1, SMC1A, SMC3, SRSF2, STAG2, TET2, TP53, U2AF 1, WT1 and ZRSR2.

DETAILED DESCRIPTION OF THE INVENTION

Figure 1:
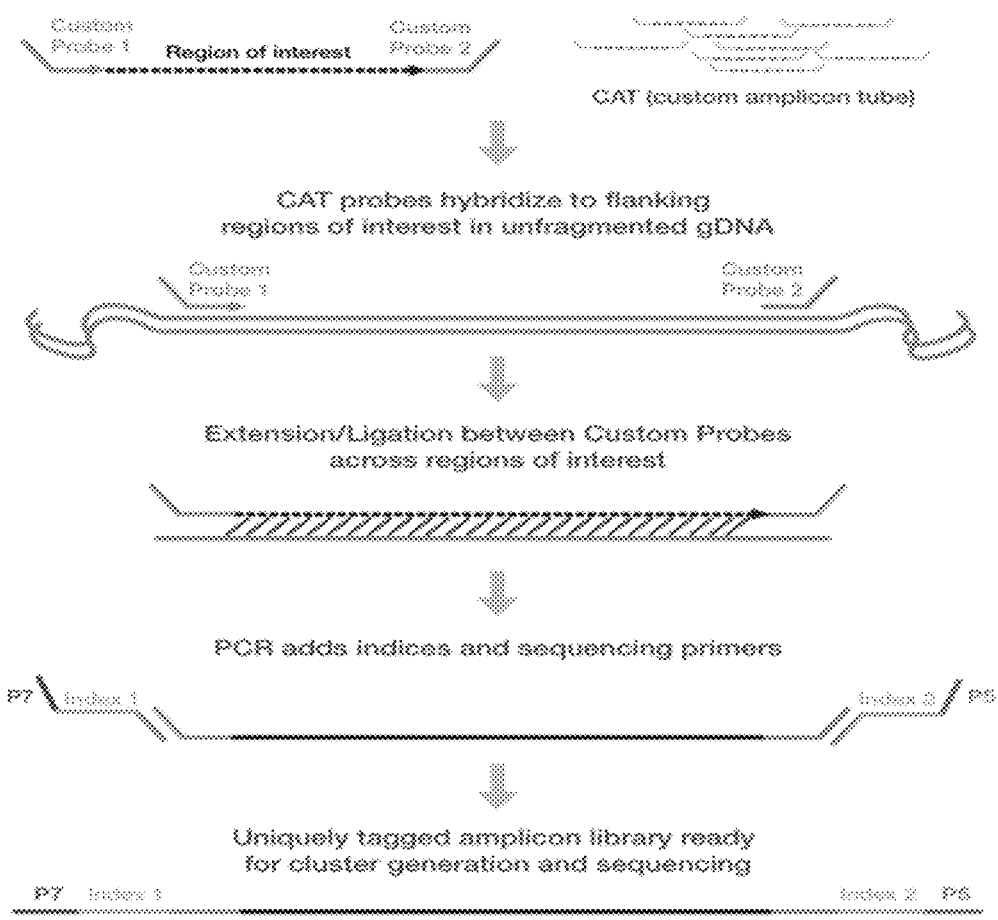
FIG. 1 illustrates an overview of a MiSeq sequencing method for detection of variants.

The present invention is based on the identification of several in-frame deletion (indel) mutations in exon 9 of the CALR gene in patients diagnosed with a myeloproliferative neoplasm. The mutations include a p.E381_A382>A deletion, a p.D397_D400>D deletion, and a p.E405_V409>V deletion. Accordingly, the invention provides variant nucleic acids with these gene mutations and the resulting mutated proteins, methods and reagents for the detection of the variants disclosed herein, uses of these variants for the development of detection reagents, and assays or kits that utilize such reagents. The invention further provides compositions and methods useful in the diagnosis, prognosis, and monitoring of hematopoietic diseases including, for example, myeloproliferative diseases.

Certain Terminology

Certain terms employed in this description have the following defined meanings. Terms that are not defined have their art-recognized meanings. That is, unless otherwise defined, all technical and scientific terms used herein have the same meaning as commonly understood by one of ordinary skill in the art to which this invention belongs.

As used herein, unless otherwise stated, the singular forms "a," "an," and "the" also include the plural. Thus, for example, a reference to "an oligonucleotide" includes a plurality of oligonucleotide molecules, a reference to label is a reference to one or more labels, a reference to "a probe" is a reference to one or more probes, and a reference to "a nucleic acid" is a reference to one or more polynucleotides.

As used herein, the term "about" when used before a numerical value, e.g., temperature, time, amount, and concentration, including range, indicates approximations which can vary by approximately ±10%, 5%, or 1%.

As used herein, the terms "isolated," "purified" or "substantially purified" refer to molecules, such as nucleic acid molecules or polypeptides, that are removed from their natural environment, isolated or separated, and are at least 60% free, preferably 75% free, and most preferably 90% free from other components with which they are naturally associated. An isolated molecule is therefore a substantially purified molecule.

A "fragment" in the context of a gene fragment or a chromosome fragment refers to a sequence of nucleotide residues which are at least or about 10 nucleotides, at least or about 20 nucleotides, at least or about 25 nucleotides, at least or about 30 nucleotides, at least or about 40 nucleotides, at least or about 50 nucleotides, at least or about 100 nucleotides, at least or about 250 nucleotides, at least or about 500 nucleotides, at least or about 1,000 nucleotides, at least or about 2,000 nucleotides.

The terms "identity" and "identical" refer to a degree of identity between sequences. There can be partial identity or complete identity. A partially identical sequence is one that is less than 100% identical to another sequence. Partially identical sequences can have an overall identity of at least 70% or at least 75%, at least 80% or at least 85%, or at least 90% or at least 95%.

The term "detectable label" as used herein refers to a molecule or a compound or a group of molecules or a group of compounds associated with a probe and is used to identify the probe hybridized to a nucleic acid molecule, such as a genomic nucleic acid molecule, an RNA nucleic acid molecule, a cDNA molecule or a reference nucleic acid.

As used herein, the term "detecting" refers to observing a signal from a detectable label to indicate the presence of a target. More specifically, detecting is used in the context of detecting a specific sequence of a target nucleic acid molecule. The term "detecting" used in context of detecting a signal from a detectable label to indicate the presence of a target nucleic acid in the sample does not require the method to provide 100% sensitivity and/or 100% specificity. A sensitivity of at least 50% is preferred, although sensitivities of at least 60%, at least 70%, at least 80%, at least 90%, or at least 99% are more preferred. A specificity of at least 50% is preferred, although sensitivities of at least 60%, at least 70%, at least 80%, at least 90%, or at least 99% are more preferred. Detecting also encompasses assays that produce false positives and false negatives. False negative rates can be 1%, 5%, 10%, 15%, 20% or even higher. False positive rates can be 1%, 5%, 10%, 15%, 20% or even higher.

As used herein, the terms "amplification" and "amplify" encompass all methods for copying or reproducing a target nucleic acid molecule having a specific sequence, thereby increasing the number of copies or amount of the nucleic acid sequence in a sample. The amplification can be exponential or linear. The target nucleic acid can be DNA or RNA. A target nucleic acid amplified in this manner is referred to herein as an "amplicon." While illustrative methods described herein relate to amplification using the polymerase chain reaction (PCR), numerous other methods are known in the art for amplification of nucleic acids, such as, but not limited to, isothermal methods, rolling circle methods, etc. The skilled artisan understands that these other methods can be used either in place of, or in conjunction with, PCR methods. See, e.g., Saiki, "Amplification of Genomic DNA" in PCR Protocols, Innis et al., Eds., Academic Press, San Diego, Calif. 1990, pp 13-20; Wharam, et al., *Nucleic Acids Res.* 2001 Jun. 1; 29(11):E54-E54; Hafner, et al., *Biotechniques* 2001 April; 30(4):852-6, 858, 860; Zhong, et al., *Biotechniques* 2001 April; 30(4):852-6, 858, 860.

As used herein, the term "oligonucleotide" refers to a short nucleic acid polymer composed of deoxyribonucleotides, ribonucleotides, or any combination thereof. Oligonucleotides are generally between about 10, 11, 12, 13, 14, 15, 16, 17, 18, 19, 20, 25, or 30 to about 150 nucleotides (nt) in length, more preferably about 10, 11, 12, 13, 14, 15, 16, 17, 18, 19, 20, 25, or 30 to about 70 nt in length. An oligonucleotide can be used as a primer or as a probe according to methods described herein and known generally in the art.

As used herein, an oligonucleotide that is "specific" for a nucleic acid is one that, under the appropriate hybridization or washing conditions, is capable of hybridizing to the target of interest and not substantially hybridizing to nucleic acids that are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well-known in the art. In some embodiments, oligonucleotides are specific for CALR genomic sequences that flank the CALR sequence encoding target deletion mutation. In some embodiments, oligonucleotides are specific for CALR deletion mutation (e.g. allele specific) and do not hybridize to a wild-type CALR sequence. For example, in some embodiments the oligonucleotides that are specific for the CALR deletion mutation span the junction between the 5' end and the 3' end of the deletion. In some embodiments, oligonucleotides are specific for CALR sequences within exon 9. In some embodiments, oligonucleotides are designed to amplify a CALR coding region only if the deletion mutation is present.

A "primer" for nucleic acid amplification is an oligonucleotide that specifically anneals to a target nucleotide sequence and leads to addition of nucleotides to the 3' end of the primer in the presence of a DNA or RNA polymerase. As known in the art, the 3' nucleotide of the primer should generally be identical to the target nucleic acid sequence at a corresponding nucleotide position for optimal expression and amplification. The term "primer" as used herein includes all forms of primers that can be synthesized including, but not limited to, peptide nucleic acid primers, locked nucleic acid primers, phosphorothioate modified primers, labeled primers, and the like. Primers can be naturally occurring as in a purified from a biological sample or from a restriction digest or produced synthetically. In some embodiments, primers can be approximately 15-100 nucleotides in length, typically 15-25 nucleotides in length. The exact length of the primer will depend upon many factors, including hybridization and polymerization temperatures, source of primer and the method used. For example, for diagnostic applications, depending on the complexity of the target sequence, the oligonucleotide primer typically contains 15-25 or more nucleotides, although it may contain fewer or more nucleotides. The factors involved in determining the appropriate length of primer are readily known to one of ordinary skill in the art. One of skill in the art understands that the terms "forward primer" and "reverse primer" refer generally to primers complementary to sequences that flank the target nucleic acid and are used for amplification of the target nucleic acid. Generally, a "forward primer" is a primer that is complementary to the anti-sense strand of DNA, and a "reverse primer" is complementary to the sense-strand of DNA.

As used herein, a "probe" refers to a type of oligonucleotide having or containing a sequence which is complementary to another polynucleotide, e.g., a target polynucleotide or another oligonucleotide. The probes for use in the methods described herein are ideally less than or equal to 500 nucleotides in length, typically between about 10 nucleotides to about 100, e.g. about 15 nucleotides to about 40 nucleotides. The probes for use in the methods described herein are typically used for detection of a target nucleic acid sequence by specifically hybridizing to the target nucleic acid. Target nucleic acids include, for example, a genomic nucleic acid, an expressed nucleic acid, a reverse transcribed nucleic acid, a recombinant nucleic acid, a synthetic nucleic acid, an amplification product or an extension product as described herein.

The term "multiplex PCR" as used herein refers to an assay that provides for simultaneous nucleic acid amplification and detection of two or more amplicons within the same reaction vessel. Each target nucleic acid is primed using a distinct primer pair. A multiplex reaction can further include specific probes for each amplicon that are detectably labeled with detectable moieties for distinguishing the amplicons. In some embodiments, the probes for each amplicon are detectably labeled with different detectable moieties. In some embodiments, the probes for each amplicon are detectably labeled with the same detectable moiety. In some embodiments, the detectable moiety is linked to the specific probe in a way that allows for selective removal of the detectable moiety.

The term "nested polymerase chain reaction" is a modification of polymerase chain reaction which involves two sets of primers, used in two successive runs of polymerase chain reaction, the second set intended to amplify the target from the first run product.

The term "complement" "complementary" or "complementarity" with reference to polynucleotides (i.e., a sequence of nucleotides such as an oligonucleotide or a target nucleic acid) refers to standard Watson/Crick pairing rules. The complement of a nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in natural nucleic acids can be included in the nucleic acids described herein; these include, for example, inosine, 7-deazaguanine, Locked Nucleic Acids (LNA), and Peptide Nucleic Acids (PNA). Complementary need not be perfect; stable duplexes can contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, detecting a mutation in a gene or protein can be accomplished by performing an appropriate assay. To detect a mutation in a gene or protein in a biological sample, the biological sample is assayed to determine the presence or absence of the mutated gene or mutated protein. The assay can include extracting nucleic acid (such as, for example, total genomic DNA and/or RNA) from the sample and analyzing the extracted nucleic acid by methods known in the art. An assay can involve isolating protein from the biological sample and analyzing the protein. However, an assay need not involve either extraction of nucleic acid or isolation of protein. That is, some assays can be employed that directly analyze a biological sample without extracting or isolating nucleic acid or protein.

As used herein, the term "subject" or "individual" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like).

As used herein, the term "sample" or "test sample" refers to any liquid or solid (or both) material can be used to test for the presence of nucleic acids. In some embodiments, a test sample is biological sample such as a cell or tissue, or a portion or fraction thereof. A biological sample can comprise a clinical sample (i.e., obtained directly from a patient) or isolated nucleic acids. In some embodiments, a sample is obtained from a tissue or bodily fluid collected from a subject. Sample sources include, but are not limited to, bodily fluids, such as, but not limited to, whole blood or isolated blood cells of any type (e.g., myeloid cells, lymphocytes), plasma, serum, sputum (processed or unprocessed), cerebrospinal fluid (CSF), pleural fluid, tears, lactal duct fluid, lymph, urine, saliva, amniotic fluid, or semen, bronchial alveolar lavage (BAL), bronchial wash (BW), or tissues (e.g., biopsy material). A sample can be a fluid and/or tissue (e.g., a biopsy) sample that is cellular (i.e. contains whole cells) or acellular (i.e. does not contain whole cells). An "acellular bodily fluid" includes less than about 1% (w/w) whole cellular material. Plasma or serum are examples of acellular bodily fluids. A sample can include a specimen of natural or synthetic origin. Exemplary sample tissues include, but are not limited to bone marrow or tissue (e.g. biopsy material). Methods of obtaining test samples and reference samples are well-known to those of skill in the art and include, but are not limited to, aspirations, tissue sections, drawing of blood or other fluids, surgical or needle biopsies, collection of paraffin embedded tissue, collection of body fluids, collection of stool, and the like. In the present context, the biological sample preferably is a blood, serum or plasma sample. The term "patient sample" as used herein refers to a sample obtained from a human seeking diagnosis and/or treatment of a disease, especially a myeloproliferative disease. In some embodiments, the sample is derived from a subject having or suspected of having a CALR-related disease or condition. In some embodiments, the sample is derived from a subject having or suspected of having a JAK2-related disease or condition. In some embodiments, the sample is derived from a subject that has received one or more treatments for a JAK2-related disease or condition or a CALR-related disease or condition. In some embodiments, the CALR-related or JAK2-related disease or condition is a myeloproliferative disease.

As used herein, the terms "CALR gene" refers to the calreticulin gene, which encodes the calreticulin protein. As used herein, the term can refer to any nucleic acid encoding a CALR protein, such as genomic DNA, mRNA, cDNA, or other engineered/recombinant nucleic acid, or portions thereof. The term encompasses, the nucleic acid sequence set forth in NCBI Accession Number NM_004343.3 (SEQ ID NO: 3) or the coding region thereof (SEQ ID NO: 1), as well as natural and engineered isoforms and variants. The term includes RNA transcripts including all or a portion of SEQ ID NO: 1, genomic sequences encoding SEQ ID NO: 1, and all untranslated CALR genomic sequence, such as, for example, introns, untranslated leader regions, and polyadenylation signals. Illustrative nucleic acid sequences encompassed by the term are publicly available at National Center for Biotechnology Information, Bethesda, Md. (www.ncbi.nlm.nih.gov) and HUGO Gene Nomenclature Committee, Cambridge, UK (www.genenames.org).

As used herein, the term "CALR protein" refers generally to the calriticulin protein, also known in the art as Sicca Syndrome Antigen A, Autoantigen Ro, endoplasmic reticulum resident protein 60 (ERp60), CRP55, HACBP, grp60, HEL-S-99n, cC1qR, calregulin, or Epididymis Secretory Sperm Binding Protein Li99n. As used herein, the term can refer to any CALR protein, polypeptide, or a portion thereof. The term encompasses the amino acid sequence set forth in NCBI Accession Number NP_004334.1 (SEQ ID NO: 2) and encoded by SEQ ID NO:1, as well as natural and engineered isoforms and variants. Exemplary CALR proteins included, but are not limited to, NP_004334 (*H. sapiens*) (SEQ ID No: 2), XP_003316194 (*P. troglodytes*) (SEQ ID No: 4), NP_001248060 (*M. mulatta*) (SEQ ID No: 5), XP_867310.2 (*C. lupus*) (SEQ ID No: 6), NP_776425.1 (*B. taurus*) (SEQ ID No: 7), NP_031617.1 (*M. musculus*) (SEQ ID No: 8), and NP_071794.1 (*R. norvegicus*) (SEQ ID No: 9).

As used herein, the term "CALR mutant" refers generally to CALR nucleic acid or amino acid sequences that differ from the wild-type sequence such as set forth, for example, in SEQ ID NO: 1 and SEQ ID NO: 2. The term includes all manner of mutations known in the art, including, but not limited to, insertions, deletions, substitutions, and inversions, encompasses both silent mutations and those that alter CALR function, and encompasses gain-of-function and loss-of-function mutations. In some embodiments described herein, CALR mutations comprise p.E381_A382>A, p.D397_D400>D, or a p.E405_V409>V deletion.

CALR nucleic acid and protein sequences described herein can be isolated from any source, including, but not limited to, a human patient, a laboratory animal or veterinary animal (e.g., dog, pig, cow, horse, rat, mouse, etc.), a sample therefrom (e.g. tissue or body fluid, or extract thereof), or a cell therefrom (e.g., primary cell or cell line, or extract thereof).

The term "p.E381_A382>A deletion" refers to a mutation in the CALR gene in which the nucleotides corresponding to nucleotides AGG at position at genome position chr19: g.13054615_13054617 (reference to GRCh37/hg19) are deleted (corresponding to nucleotides 1142-1144 of the CALR nucleotide coding sequence of SEQ ID NO: 1). This in-frame insertion/deletion (indel) mutation results in the p.E381_A382>A deletion mutation in the CALR protein in which the dipeptide glutamic acid-alanine (EA) at amino acid positions 381-382 of SEQ ID NO: 2 is deleted and replaced by alanine (A).

The term "p.D397_D400>D deletion" refers to a mutation in the CALR gene in which the nucleotides corresponding to nucleotides TGAGGAGGA at genome position chr19: g.13054664_13054672 (reference to GRCh37/hg19) are deleted (corresponding to nucleotides 1182-1190 of the CALR nucleotide coding sequence of SEQ ID NO: 1). This in-frame insertion/deletion (indel) mutation results in the p.D397_D400>D deletion mutation in the CALR protein in which the tetrapeptide DEED (SEQ ID NO: 15) at amino acid positions 397-400 of SEQ ID NO: 2 is deleted and replaced by aspartic acid (D).

The term "p.E405_V409>V deletion" refers to a mutation in the CALR gene in which the nucleotides corresponding to nucleotides AGGAGGAAGATG (SEQ ID NO: 16) at genome position chr19:g.13054687_13054698 (reference to GRCh37/hg19) are deleted (corresponding to nucleotides 1214-1225 of the CALR nucleotide coding sequence of SEQ ID NO: 1). This in-frame insertion/deletion (indel) mutation results in the p.E405_V409>V deletion mutation in the CALR protein in which the pentapeptide EEEDV (SEQ ID NO: 17) at amino acid positions 405-409 of SEQ ID NO: 2 is deleted and replaced by valine (V).

The term "zygosity status" as used herein means whether an individual is homozygous for a gene or gene mutation, i.e. both alleles have the same copy of a gene or gene mutation, or heterozygous for a gene or gene mutation, i.e. only one allele has a copy of the gene or gene mutation.

The terms "myeloproliferative disease (MPD)" and "myeloproliferative neoplasm (MPN)" or "myeloproliferative disorder" are used herein interchangeably to mean non-lymphoid dysplastic or neoplastic conditions arising from a hematopoietic stem cell or its progeny. A myeloproliferative disease is generally manifest by abnormal cell division resulting in an abnormal level of a particular hematological cell population. The abnormal cell division underlying a proliferative hematological disorder is typically inherent in the cells and not a normal physiological response to infection or inflammation. Exemplary myeloproliferative diseases include, but are not limited to, polycythemia vera (PV), essential thrombocythemia (ET) and idiopathic myelofibrosis (IMF). Also included in the definition as used herein are acute myeloid leukemia (AML), myelodysplastic syndrome (MDS), chronic myelogenous leukemia (CIVIL), hypereosinophilic syndrome (HES), chronic neutrophilic leukemia (CNL), myelofibrosis with myeloid metaplasia (MMM), chronic myelomonocytic leukemia (CMML), juvenile myelomonocytic leukemia, chronic basophilic leukemia, chronic eosinophilic leukemia, systemic mastocytosis (SM) and unclassified myeloproliferative diseases (UMPD or MPD-NC).

The term "diagnose" or "diagnosis" or "diagnosing" as used herein refer to distinguishing or identifying a disease, syndrome or condition or distinguishing or identifying a person having a particular disease, syndrome or condition. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there can be differential diagnoses that can be inferred from a diagnostic factor or symptom. Likewise, there can be instances where a factor or symptom that is indicative of a particular disease is present in an individual that does not have the particular disease.

The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease.

The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis can be expressed as the amount of time a patient can be expected to survive. Alternatively, a prognosis can refer to the likelihood that the disease goes into remission or to the amount of time the disease can be expected to remain in remission. Prognosis can be expressed in various ways; for example prognosis can be expressed as a percent chance that a patient will survive after one year, five years, ten years or the like. Alternatively prognosis can be expressed as the number of years, on average that a patient can expect to survive as a result of a condition or disease. The prognosis of a patient can be considered as an expression of relativism, with many factors effecting the ultimate outcome. For example, for patients with certain conditions, prognosis can be appropriately expressed as the likelihood that a condition can be treatable or curable, or the likelihood that a disease will go into remission, whereas for patients with more severe conditions prognosis can be more appropriately expressed as likelihood of survival for a specified period of time.

The term "poor prognosis" as used herein, in the context of a patient having a myeloproliferative disease and a mutation in the CALR gene, refers to an increased likelihood that the patient will have a worse outcome in a clinical condition relative to a patient diagnosed as having the same disease but without the mutation. A poor prognosis can be expressed in any relevant prognostic terms and can include, for example, the expectation of a reduced duration of remission, reduced survival rate, and reduced survival duration.

As used herein, the term "specifically binds," when referring to a binding moiety, is meant that the moiety is capable of discriminating between a various target sequences. For example, an oligonucleotide (e.g., a primer or probe) that specifically binds to a mutant target sequence is one that hybridizes preferentially to the target sequence (e.g., the wild-type sequence) over the other sequence variants (e.g., mutant and polymorphic sequences). Preferably, oligonucleotides specifically bind to their target sequences under high stringency hybridization conditions.

As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the Tm of the formed hybrid.

As used herein the term "stringency" is used in reference to the conditions of temperature, ionic strength, and the presence of other compounds, under which nucleic acid hybridizations are conducted. With high stringency conditions, nucleic acid base pairing will occur only between nucleic acids that have sufficiently long segment with a high frequency of complementary base sequences.

Exemplary hybridization conditions are as follows. High stringency generally refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5×SSC (saline sodium citrate) 0.2% SDS (sodium dodecyl sulphate) at 42° C., followed by washing in 0.1×SSC, and 0.1% SDS at 65° C. Moderate stringency refers to conditions equivalent to hybridization in 50% formamide, 5×Denhardt's solution, 5×SSC, 0.2% SDS at 42° C., followed by washing in 0.2×SSC, 0.2% SDS, at 65° C. Low stringency refers to conditions equivalent to hybridization in 10% formamide, 5×Denhardt's solution, 6×SSC, 0.2% SDS, followed by washing in 1×SSC, 0.2% SDS, at 50° C.

CALR Indel Mutations

Provide herein are methods for the detection of in-frame deletion mutations in exon 9 of the CALR gene. In some embodiments, the CALR gene comprises an nucleic acid deletion at genome position chr19:g.13054615_13054617 (reference to GRCh37/hg19) (corresponding to nucleotides 1142-1144 of the CALR nucleotide coding sequence of SEQ ID NO: 1). For example, in one embodiment, the mutation results in a CALR protein, wherein E381 and A382 of SEQ ID NO:2 are replaced with alanine (A) alone. In some embodiments, the CALR gene comprises an nucleic acid deletion at genome position chr19:g.13054664_13054672 (reference to GRCh37/hg19) (corresponding to nucleotides 1182-1190 of the CALR nucleotide coding sequence of SEQ ID NO: 1). For example, in one embodiment, the mutation results in a CALR protein, wherein D397, E398, E399, and D400 of SEQ ID NO:2 are replaced with aspartic acid (D) alone. In some embodiments, the CALR gene comprises an nucleic acid deletion at genome position chr19: g.13054687_13054698 (reference to GRCh37/hg19) are deleted (corresponding to nucleotides 1214-1225 of the CALR nucleotide coding sequence of SEQ ID NO: 1). For example, in one embodiment, the mutation results in a CALR protein, wherein E405, E406, E407, D408, and V409 of SEQ ID NO:2 are replaced with valine (V) alone. In some embodiments, the methods further comprise detection of one or more additional mutations in the CALR gene. In some embodiments, the methods further comprise detection of one or more additional mutations in the one or more additional genes. In some embodiments, the one or more additional genes is associated with a myeloproliferative disorder.

p.E381_A382>A Deletion Mutation

In some embodiments provided herein, the p.E381_A382>A indel mutation in the CALR gene is detected in a sample containing a CALR nucleic acid. The CALR nucleic acid is assessed by any suitable method including, for example, by nucleic acid sequencing or oligonucleotide hybridization. For example, the p.E381_A382>A indel mutation can be assessed by amplifying a target sequence of an CALR nucleic acid (e.g., genomic DNA, RNA, or cDNA) containing all or a portion of the mutation. Relatedly, detection of the p.E381_A382>A indel mutation can involve using probes and/or primers capable of specifically hybridizing to the mutation site. One suitable target nucleic acid sequence from the CALR gene for assessing the presence of this mutation comprises all or a portion of exon 9 of CALR. In some embodiments the target nucleic acid sequence comprises a nucleic acid corresponding to genome position chr19.13054525-13054728. In some embodiments the target nucleic acid sequence comprises a nucleic acid corresponding to genome position chr19:g.13054615_13054617. Target sequences (including primer and probe sequences encompassing this mutation) can be of any suitable length (e.g., 20, 25, 30, 35, 40, 50, 100, 200, 300, or more nucleotides in length). The nucleic acid can be DNA and/or RNA.

Alternatively, the presence of the p.E381_A382>A indel mutation can be assessed by evaluating the CALR protein present in a patient sample such as by specifically detecting the p.E381_A382>A CALR protein variant. CALR protein assessment can be performed by any appropriate method including amino acid sequencing or through the use of mutant CALR-specific antibodies (e.g., using an ELISA). Mutant CALR proteins can be assessed by amino acid sequencing of all or a portion of the CALR protein comprising the variant. Optionally, antibodies (polyclonal or monoclonal) can be raised against a polypeptide epitope having the sequence of all or a portion of the CALR protein comprising the variant.

Additional methods for the detection of mutant nucleic acids and/or the encoded mutant proteins are provided elsewhere herein and can be employed for the detection of the p.E381_A382>A indel mutation.

p.D397_D400>D Deletion Mutation

In some embodiments provided herein, the p.D397_D400>D indel mutation in the CALR gene is detected in a sample containing a CALR nucleic acid. The CALR nucleic acid is assessed by any suitable method including, for example, by nucleic acid sequencing or oligonucleotide hybridization. For example, the p.D397_D400>D indel mutation can be assessed by amplifying a target sequence of an CALR nucleic acid (e.g., genomic DNA, RNA, or cDNA) containing all or a portion of the mutation. Relatedly, detection of the p.D397_D400>D indel mutation can involve using probes and/or primers capable of specifically hybridizing to the mutation site. In some embodiments the target nucleic acid sequence comprises a nucleic acid corresponding to genome position chr19.13054525-13054728. In some embodiments the target nucleic acid sequence comprises a nucleic acid corresponding to genome position chr19:g.13054664_13054672. Target sequences (including primer and probe sequences encompassing this mutation) can be of any suitable length (e.g., 20, 25, 30, 35, 40, 50, 100, 200, 300, or more nucleotides in length). The nucleic acid can be DNA and/or RNA.

Alternatively, the presence of the p.D397_D400>D indel mutation can be assessed by evaluating the CALR protein present in a patient sample such as by specifically detecting the p.D397_D400>D CALR protein variant. CALR protein assessment can be performed by any appropriate method including amino acid sequencing or through the use of mutant CALR-specific antibodies (e.g., using an ELISA). Mutant CALR proteins can be assessed by amino acid sequencing of all or a portion of the CALR protein comprising the variant. Optionally, antibodies (polyclonal or monoclonal) can be raised against a polypeptide epitope having the sequence of all or a portion of the CALR protein comprising the variant.

Additional methods for the detection of mutant nucleic acids and/or the encoded mutant proteins are provided elsewhere herein and can be employed for the detection of the p.D397_D400>D indel mutation.

p.E405_V409>V Deletion Mutation

In some embodiments provided herein, the p.E405_V409>V indel mutation in the CALR gene is detected in a sample containing a CALR nucleic acid. The CALR nucleic acid is assessed by any suitable method including, for example, by nucleic acid sequencing or oligonucleotide hybridization. For example, the p.E405_V409>V indel mutation can be assessed by amplifying a target sequence of an CALR nucleic acid (e.g., genomic DNA, RNA, or cDNA) containing all or a portion of the mutation. Relatedly, detection of the p.E405_V409>V indel mutation can involve using probes and/or primers capable of specifically hybridizing to the mutation site. In some embodiments the target nucleic acid sequence comprises a nucleic acid corresponding to genome position chr19.13054525-13054728. In some embodiments the target nucleic acid sequence comprises a nucleic acid corresponding to genome position chr19:g.13054687_13054698. Target sequences (including primer and probe sequences encompassing this mutation) can be of any suitable length (e.g., 20, 25, 30, 35, 40, 50, 100, 200, 300, or more nucleotides in length). The nucleic acid can be DNA and/or RNA.

Alternatively, the presence of the p.E405_V409>V indel mutation can be assessed by evaluating the CALR protein present in a patient sample such as by specifically detecting the p.E405_V409>V CALR protein variant. CALR protein assessment can be performed by any appropriate method including amino acid sequencing or through the use of mutant CALR-specific antibodies (e.g., using an ELISA). Mutant CALR proteins can be assessed by amino acid sequencing of all or a portion of the CALR protein comprising the variant. Optionally, antibodies (polyclonal or monoclonal) can be raised against a polypeptide epitope having the sequence of all or a portion of the CALR protein comprising the variant.

Additional methods for the detection of mutant nucleic acids and/or the encoded mutant proteins are provided elsewhere herein and can be employed for the detection of the p.E405_V409>V indel mutation.

JAK-STAT Pathway Mutations

As described herein, indel mutations in CALR exon 9 are associated with a higher frequency of somatic mutations in genes that encode proteins that participate in the JAK-STAT pathway, particularly in patients that have a myeloproliferative disease. In some embodiments provided herein, detection of a CALR indel exon 9 mutation in a subject indicates a higher probability that the subject will develop a somatic mutation in genes that encode proteins involved in myeloproliferative disease. In particular cases, the somatic mutation occurs in genes that encode a JAK-STAT pathway protein. In some embodiments, the genes that is mutated is JAK2, MPL, CSFR3R, ASXL1, or ZRSR2. In some embodiments a mutation is located in exon 12 of JAK2, exon 10 of MPL or exon 14 or exon 17 CSFR3R. In some embodiments, the mutation is JAK2 V617F, MPL W515L, CSFR3R A470T, ASXL1 D954fs*26, or ZRSR2 S449_R450du (c.1338_1343dupGGCCG).

Accordingly, provided herein are methods for detecting one or more additional mutations in one or more additional genes associated with a myeloproliferative disorder. In some embodiments, the gene encodes a JAK-STAT pathway protein. In some embodiments a mutation in JAK2, MPL, CSFR3R, ASXL1, or ZRSR2 is detected. In some embodiments a mutation in exon 12 of JAK2, in exon 14 of JAK2, exon 10 of MPL or exon 14 or exon 17 CSFR3R is detected. In some embodiments, a BCR-ABL1 translocation is detected. In some embodiments, a mutation that is JAK2 V617F, MPL W515L, CSFR3R A470T, ASXL1 D954fs*26, or ZRSR2 S449_R450du is detected. (c.1338_1343dupGGCCG). In some embodiments, a translocation involving FGFR1, PDGFRA, or PDGFRB is detected. In some embodiments, the additional mutation is a mutation in JAK2 as disclosed in Table 2 of U.S. Pat. No. 8,512,948.

In some embodiments, the additional variant for detection with a CALR mutant described herein is selected from a variant in a gene selected from among ASXL1, CALR, CBL, CEBPA, CSF3R, DDX41, DNMT3A, EZH2, FLT3, GATA1, IDH1, IDH2, JAK2, KDM6A, KIT, KRAS, MLL, MPL, NPM1, NRAS, PTPN11, RUNX1, SETBP1, SF3B1, SRSF2, TET2, TP53, U2AF1, WT1 and ZRSR2. In some embodiments, the additional variant for detection with a CALR mutant described herein is selected from a variant in an exon disclosed in Table 1.

In some embodiments, the additional variant for detection with a CALR mutant described herein is selected from a variant in a gene selected from among ABL1, ASXL1, ATRX, BCOR, BCORL1, BRAF, CALR, CBL, CBLB, CBLC, CDKN2A, CEBPA, CSF3R, CUX1, DDX41, DNMT3A, ETV6/TEL, EZH2, FBXW7, FLT3, GATA1, GATA2, GNAS, HRAS, IDH1, IDH2, IKZF1, JAK2, JAK3, KDM6A, KIT, KRAS, MLL, MPL, MYD88, NOTCH1, NPM1, NRAS, PDGFRA, PHF6, PTPN11, RAF21, RUNX1, SETBP1, SF3B1, SMC1A, SMC3, SRSF2, STAG2, TET2, TP53, U2AF1, WT1 and ZRSR2.

In some embodiments, an additional mutation in the CALR gene is detected. In some embodiments, the additional mutation is an additional mutation in exon 9 of the CALR gene. In some embodiments, the additional mutation is a +1 frameshift mutation in the CALR gene.

In some embodiments, the methods include monitoring patients having an indel mutations in CALR exon 9 for the development of a somatic mutation in a gene involved in a myeloproliferative disease. In some embodiments, the gene encodes a JAK-STAT pathway protein. In some embodiments, the patient has a myeloproliferative disease.

In some embodiments, the methods include monitoring patients being treated for a myeloproliferative disease for the development of an indel mutation in CALR exon 9. In some embodiments, the methods include monitoring patients being treated for a myeloproliferative disease for the development of an indel mutation in CALR exon 9 and one or more mutations in a JAK-STAT pathway gene, including, but not limited to, JAK2, MPL, CSFR3R, ASXL1, or ZRSR2. Accordingly, the methods can be employed as a companion diagnostic for detection of a CALR exon 9 indel mutation in a subject that has received one or more treatments for a myeloproliferative disease, such as polycythemia vera, essential thrombocythemia, idiopathic myelofibrosis, and unclassified myeloproliferative disease.

Sample Collection and Preparation

The methods and compositions of the present invention can be used to detect mutations in the CALR gene and other mutations described herein using a biological sample obtained from an individual. Samples can be obtained from patients suspected of having a mutated nucleic acid sequence, for example, from a tissue of fluid sample containing tumor cells or cancer cells. The methods provided can be performed using any sample containing nucleic acid. In some embodiments, the nucleic acid is deoxyribonucleic acid (DNA). In some embodiments, the nucleic acid is ribonucleic acid (RNA). The sample can be processed to release or otherwise make available a nucleic acid for detection as described herein. The nucleic acid (e.g., DNA or RNA) can be isolated from the sample according to any methods well-known to those of skill in the art. Such processing can include steps of nucleic acid manipulation, e.g., preparing a cDNA by reverse transcription of RNA from the biological sample. Thus, the nucleic acid to be assayed by the methods of the invention can be genomic DNA, cDNA, single stranded DNA or mRNA.

Examples of biological samples include tissue samples or any cell-containing or acellular bodily fluids. Biological samples can be obtained by standard procedures and can be used immediately or stored, under conditions appropriate for the type of biological sample, for later use.

In some embodiments, the methods provided herein can be applied to any type of tissue from a patient. Sources of such tissue include but are not limited to nervous system, thyroid, skin, gastrointestinal tract, large intestine, biliary tract, ovary, eye, prostate, central nervous system, liver, small intestine, breast, pancreas, soft tissue, digestive tract, adrenal gland, autonomic ganglia, hematopoietic and lymphoid tissue, lung, esophagus, pituitary, and stomach.

In some embodiments, the methods can be applied over a wide range of tumor types. In some embodiments, the methods of the invention are applied to samples from patients having a myeloproliferative neoplam. In some embodiments, the methods of the invention are applied to blood samples from patients having a myeloproliferative neoplam.

Methods of obtaining test samples are well-known to those of skill in the art and include, but are not limited to, aspirations, tissue sections, drawing of blood or other fluids, surgical or needle biopsies, and the like. The test sample can be obtained from an individual or patient diagnosed as having a myeloproliferative disorder or suspected being afflicted with a myeloproliferative disorder. In some embodiments, the test sample is obtained from an individual or patient that has received one or more treatments for a myeloproliferative disorder. The test sample can be a cell-containing liquid or a tissue. Samples can include, but are not limited to, amniotic fluid, biopsies, blood, blood cells, bone marrow, fine needle biopsy samples, peritoneal fluid, amniotic fluid, plasma, pleural fluid, saliva, semen, serum, tissue or tissue homogenates, frozen or paraffin sections of tissue. Samples can also be processed, such as sectioning of tissues, fractionation, purification, or cellular organelle separation.

If necessary, the sample can be collected or concentrated by centrifugation and the like. The cells of the sample can be subjected to lysis, such as by treatments with enzymes, heat, surfactants, ultrasonication, or a combination thereof. The lysis treatment is performed in order to obtain a sufficient amount of nucleic acid derived from the individual's cells to detect using a nucleic acid detection assay, e.g. a detection assay using PCR.

Methods of plasma and serum preparation are well-known in the art. Either "fresh" blood plasma or serum, or frozen (stored) and subsequently thawed plasma or serum can be used. Frozen (stored) plasma or serum should optimally be maintained at storage conditions of −20° C. to −70° C. until thawed and used. "Fresh" plasma or serum can be refrigerated or maintained on ice until used, with nucleic acid (e.g., RNA, DNA or total nucleic acid) extraction being performed as soon as possible. Exemplary methods are described below.

Blood can be drawn by standard methods into a collection tube, typically siliconized glass, either without anticoagulant for preparation of serum, or with EDTA, sodium citrate, heparin, or similar anticoagulants for preparation of plasma. If preparing plasma or serum for storage, plasma or serum can be first fractionated from whole blood prior to being frozen. This reduces the burden of extraneous intracellular RNA released from lysis of frozen and thawed cells which might reduce the sensitivity of the amplification assay or interfere with the amplification assay through release of inhibitors such as porphyrins and hematin that inhibit nucleic acid amplification (e.g., PCR). "Fresh" plasma or serum can be fractionated from whole blood by centrifugation, using gentle centrifugation at 300-800 times gravity for five to ten minutes, or fractionated by other standard methods. High centrifugation rates capable of fractionating out apoptotic bodies are generally avoided. Since heparin can interfere with reverse transcription and nucleic acid amplification, use of heparinized blood can require pretreatment with heparanase, followed by removal of calcium prior to reverse transcription or amplification. Imai, H. et al. *J. Virol. Methods* 36:181-184, (1992). In some embodiments, EDTA is a suitable anticoagulant for blood specimens for which nucleic acid amplification (e.g., PCR) is subsequently performed.

Nucleic Acid Extraction and Amplification

The nucleic acid to be assayed can be assayed directly from a biological sample or extracted from the biological sample prior to detection. As described herein, the biological sample can be any sample that contains a nucleic acid molecule, such as a fluid sample, a tissue sample, or a cell sample. The biological sample can be from a subject which includes any animal, preferably a mammal. A preferred subject is a human, which can be a patient presenting to a medical provider for diagnosis or treatment of a disease. The volume of plasma or serum used in the extraction can be varied dependent upon clinical intent, but volumes of 100 μL to one milliliter of plasma or serum are usually sufficient.

Various methods of extraction are suitable for isolating the DNA or RNA. In general, the aim is to separate DNA present in the nucleus of the cell from other cellular components. The isolation of nucleic acid usually involves lysis of tissue or cells. This process is essential for the destruction of protein structures and allows for release of nucleic acids from the nucleus. Lysis is typically carried out in a salt solution, containing detergents to denature proteins or proteases (enzymes digesting proteins), such as Proteinase K, or in some cases both. It results in the breakdown of cells and dissolving of membranes. Methods of DNA isolation include, but are not limited to, phenol: chloroform extraction, high salt precipitation, alkaline denaturation, ion exchange column chromatography, resin binding, and paramagnetic bead binding. See, e.g. Maniatis et al., Molecular Cloning, A Laboratory Manual, 2d, Cold Spring Harbor Laboratory Press, page 16.54 (1989). Numerous commercial kits that yield suitable DNA and RNA include, but are not limited to, QIAamp™ mini blood kit, Agencourt Genfind™, Roche Cobas®, Roche MagNA Pure®, or phenol:chloroform extraction using Eppendorf Phase Lock Gels®, and the NucliSens extraction kit (Biomerieux, Marcy l'Etoile, France).

Methods of RNA isolation known to those skilled in the art are also utilized. RNA can be isolated and prepared for hybridization by a variety of methods including, but not limited to, Trizol® and Guanidinium thiocyanate-phenol-chloroform extraction. The principle of RNA isolation is based on cell/tissue lysis, followed by extraction, precipitation, and washing. In other methods, mRNA can be extracted from patient biological samples (e.g. blood samples) using a commercial kit suitable for mRNA extraction, e.g. MagNA Pure LC mRNA HS kit and Mag NA Pure LC Instrument (Roche Diagnostics Corporation, Roche Applied Science, Indianapolis, Ind.).

Nucleic acid extracted from tissues, cells, plasma or serum can be amplified using nucleic acid amplification techniques well-known in the art. Many of these amplification methods can also be used to detect the presence of mutations simply by designing oligonucleotide primers or probes to interact with or hybridize to a particular target sequence in a specific manner (e.g., allele specific primers and/or probes or primers that flank target nucleic acids sequences). By way of example, but not by way of limitation, these techniques can include, but are not limited to, polymerase chain reaction (PCR), reverse transcriptase polymerase chain reaction (RT-PCR), real-time PCR (qPCR), nested PCR, ligase chain reaction (LCA) (see Abravaya, K., et al., *Nucleic Acids Research*, 23:675-682, (1995)), branched DNA signal amplification (Urdea, M. S., et al., *AIDS*, 7 (suppl 2):S11-S14, (1993)), amplifiable RNA reporters, Q-beta replication, transcription-based amplification system (TAS), boomerang DNA amplification, strand displacement activation (SDA), cycling probe technology, isothermal nucleic acid sequence based amplification (NASBA) (see Kievits, T. et al., *J Virological Methods*, 35:273-286, (1991)), Invader Technology, helicase dependent amplification (HDA) Amplification Refractory Mutation System (ARMS), and other sequence replication assays or signal amplification assays. Exemplary methods of amplification are described briefly below and are well-known in the art.

In some embodiments, the methods provided herein employ reverse transcription of RNA obtained from the subject to cDNA. Method of reverse transcription and amplification are well-known in the art. Exemplary reverse transcriptases that can be used, include, but are not limited to, MMLV RT, RNase H mutants of MMLV RT such as Superscript and Superscript II (Life Technologies, GIBCO BRL, Gaithersburg, Md.), AMV RT, and thermostable reverse transcriptase from *Thermus Thermophilus*. For example, one exemplary method that can be used to convert RNA extracted from plasma or serum to cDNA is the protocol adapted from the Superscript II Preamplification system (Life Technologies, GIBCO BRL, Gaithersburg, Md.; catalog no. 18089-011), as described by Rashtchian, A., *PCR Methods Applic.*, 4:S83-S91, (1994). In some embodiments, the cDNA is then used as a template for a nucleic acid amplification reaction for amplifying nucleic acids encoding the mutation.

A variety of amplification enzymes are well-known in the art and include, for example, DNA polymerase, RNA polymerase, reverse transcriptase, Q-beta replicase, thermostable DNA and RNA polymerases. Because these and other amplification reactions are catalyzed by enzymes, in a single step assay the nucleic acid releasing reagents and the detection reagents should not be potential inhibitors of amplification enzymes if the ultimate detection is to be amplification based.

PCR is a technique for exponentially making numerous copies of a specific template DNA sequence. The reaction consists of multiple amplification cycles (i.e. thermocycling) and is initiated using a pair of primer sequences that hybridize to the 5' and 3' ends of the sequence to be copied. The amplification cycle typically includes an initial denaturation (i.e. strand separation) of the target nucleic acid, typically at about 95° C., followed by up to 50 cycles or more of (1) denaturation, (2) annealing the primers to the target nucleic acid at a temperature determined by the melting point (Tm) of the region of homology between the primer and the target, and (3) extension at a temperature dependent on the polymerase, most commonly 72° C. An extended period of extension is typically performed at the end of the cycling. In each cycle of the reaction, the DNA sequence between the primers is copied. Primers can bind to the copied DNA as well as the original template sequence, so the total number of copies increases exponentially with time. PCR can be performed as according to Whelan, et al., *J of Clin Micro,* 33(3):556-561 (1995). An exemplary PCR reaction mixture includes two specific primers, dNTPs, approximately 0.25 U of thermostable polymerase, such as a Taq polymerase, and 1×PCR Buffer, typically containing a buffer (e.g. Tris), a salt (e.g. KCl) and magnesium ($MgCl_2$). The Tm of a primer varies according to the length, G+C content, and the buffer conditions, among other factors. As used herein, Tm refers to that in the buffer used for the reaction of interest.

Cycling parameters for amplification can be varied, depending on the length of nucleic acids to be extended. The skilled artisan is capable of designing and preparing primers that are appropriate for amplifying a target sequence in view of this disclosure. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to the person of ordinary skill. For example, the length of a short nucleic acid or oligonucleotide can relate to its hybridization specificity or selectivity LCR is a method of DNA amplification similar to PCR, except that it uses four primers instead of two and uses the enzyme ligase to ligate or join two segments of DNA. LCR can be performed as according to Moore et al., *J Clin Micro,* 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS,* 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., *J Clin Micro,* 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µA TMA reaction mixture is placed in a tube, 200 µA oil reagent is added and amplification is accomplished by incubation at 42° C. in a water bath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.,* 26(9):2250-2251 (1998). Briefly, an NASBA reaction mixture contains two specific primers, dNTP, NTP, 6.4 U of AMV reverse transcriptase, 0.08 U of *Escherichia coli* RNase H, and 32 U of T7 RNA polymerase. The amplification is carried out for 120 min at 41° C. in a total volume of 20 µl.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method can be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager *Eur J Biochem,* 235:256-261 (1996)).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., *PNAS,* 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo-Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 min. at 95° C.

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi, *Trends Biotechnol.* 1991 9(2):53-8, 1991).

In some embodiments, PCR is used to amplify a target or marker sequence of interest. The skilled artisan is capable of designing and preparing primers that are appropriate for amplifying a target or marker sequence. The length of the amplification primers depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill. For example, the length of a short nucleic acid or oligonucleotide can relate to its hybridization specificity or selectivity.

For analyzing mutations and other variant nucleic acids, oligonucleotides specific for alternative alleles can be used. Such oligonucleotides which detect single nucleotide variations (e.g. single nucleotide polymorphisms (SNPs)), insertions, or deletions in target sequences can be referred to by such terms as "allele-specific probes," or "allele-specific primers." The design and use of allele-specific probes for analyzing nucleotide variations is described in, for example, Mutation Detection A Practical Approach, ed. Cotton et al. Oxford University Press, 1998; Saiki et al., *Nature,* 324: 163-166 (1986); Dattagupta, EP235,726; and Saiki, WO 89/11548. In one embodiment, wherein the variant is a deletion, a probe or primer can be designed to hybridize to a segment of target DNA such that probe or primer spans the 5' to 3' junction of the deletion. In one embodiment, wherein the variant is an insertion, a probe or primer can be designed to hybridize to a segment of target DNA such that probe or primer includes all or a portion of the inserted nucleotide sequence. In one embodiment, wherein the variant is a SNP, a probe or primer can be designed to hybridize to a segment of target DNA such that the SNP aligns with either the 5' most end or the 3' most end of the probe or primer. Typically, the allele-specific probes and primers are designed to specifically hybridize to the mutation, insertion, or deletion with high stringency.

Assay controls can be used in the assay for detecting a mutated nucleic acid sequence. In some embodiments, an internal positive amplification control can be included in the sample, utilizing oligonucleotide primers and/or probes.

In some embodiments, sequences from two or more regions of interest are amplified in the same reaction vessel.

In some embodiments, the nucleic acid amplification includes a labeled primer, thereby allowing detection of the amplification product of that primer. In particular embodiments, the nucleic acid amplification includes a multiplicity of labeled primers; typically, such primers are distinguishably labeled, allowing the simultaneous detection of multiple amplification products. In some embodiments, the primers having different sequences are labeled with different detectable moieties. In other embodiments, the primers having different sequences are labeled with the same detectable moiety, and distinguished by different cleavable linkers that attach the label to the primer. Methods involving labeling primers used during the amplification step can be utilized such that the amplification products are labeled with a detectable marker and hybridizing the amplification product to oligonucleotide probes labeled with a detectable marker. Detectable markers include but are not limited to luminescent tags, fluorescent tags, and radioactive tags. Labeled amplification product can be directly measured using methods corresponding to the type of label used according to methods would be known to one skilled in the art. Labeled probes can be hybridized to the amplification product according to methods known to one skilled in the art.

In one type of PCR-based assay, an allele-specific primer hybridizes to a region on a target nucleic acid molecule that overlaps a nucleic acid sequence having a target deletion and only primes amplification of an allelic form to which the primer exhibits perfect complementarity. This primer is used in conjunction with a second primer that hybridizes at a distal site. Amplification proceeds from the two primers, producing a detectable product that indicates which allelic form is present in the test sample.

In another type of PCR-based assay, an allele-specific primer hybridizes to a region on a target nucleic acid molecule that overlaps a SNP position or deletion breakpoint site and only primes amplification of an allelic form to which the primer exhibits perfect complementarity (Gibbs, 1989, *Nucleic Acid Res.,* 17:2427-2448). Typically, the primer's 3'-most nucleotide is aligned with and complementary to the SNP position or deletion breakpoint site of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target mutation position) because this position is most destabilizing to elongation from the primer (see, e.g., WO 93/22456).

In a specific embodiment, a primer contains a sequence substantially complementary to a segment of a target mutation-containing nucleic acid molecule except that the primer has a mismatched nucleotide in one of the three nucleotide positions at the 3'-most end of the primer, such that the mismatched nucleotide does not base pair with a particular allele at the mutation site. In one embodiment, the mismatched nucleotide in the primer is the second from the last nucleotide at the 3'-most position of the primer. In another embodiment, the mismatched nucleotide in the primer is the last nucleotide at the 3'-most position of the primer.

In one embodiment, primer or probe is labeled with a fluorogenic reporter dye that emits a detectable signal. While a suitable reporter dye is a fluorescent dye, any reporter dye that can be attached to a detection reagent such as an oligonucleotide probe or primer is suitable for use in the invention. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

The present invention also contemplates reagents that do not contain (or that are complementary to) a mutated nucleotide sequence identified herein but that are used to assay one or more of the mutations disclosed herein. For example, primers that flank, but do not hybridize directly to a target position provided herein are useful in primer extension reactions in which the primers hybridize to a region adjacent to the target position (i.e., within one or more nucleotides from the target mutation site, e.g. SNP, insertion or deletion).

During the primer extension reaction, a primer is typically not able to extend past a target mutation site if a particular nucleotide (allele) is present at that target site, and the primer extension product can readily be detected in order to determine which allele (i.e., wild-type or mutant) is present. For example, particular ddNTPs are typically used in the primer extension reaction to terminate primer extension once a ddNTP is incorporated into the extension product. Thus, reagents that bind to a nucleic acid molecule in a region adjacent to a mutation site, even though the bound sequences do not necessarily include the mutation site itself, are also encompassed by the present invention.

Detection of Variant Sequences.

Variant nucleic acids can be amplified prior to detection or can be detected directly during an amplification step (i.e., "real-time" methods). In some embodiments, the target sequence is amplified and the resulting amplicon is detected by electrophoresis. In some embodiments, the specific mutation or variant is detected by sequencing the amplified nucleic acid, for example, Sanger sequencing or Next Generation Sequencing (NGS). Next-generation sequencing lowers the costs and greatly increases the speed over the industry standard dye-terminator methods. Examples of NGS include, but are not limited to, Massively Parallel Signature Sequencing (MPSS), Polony sequencing combined an in vitro paired-tag library with emulsion PCR, 454 pyrosequencing, Solexa sequencing, SOLiD technology, DNA nanoball, Heliscope single molecule, Single molecule real time (SMRT) and ion semiconductor sequencing.

In some embodiments, the target sequence is amplified using a labeled primer such that the resulting amplicon is detectably labeled. In some embodiments, the primer is fluorescently labeled. In some embodiments, at least one allele-specific primer is used (e.g. a primer the spans the deletion breakpoint site, i.e., spans the junction formed by the 5' and 3' ends of the deletion).

For the methods provided herein, a single primer can be used for detection, for example as in single nucleotide primer extension or allele-specific detection of nucleic acid containing the mutation, or a second primer can be used which can be upstream or downstream of the allele-specific primer. One or more of the primers used can be allele-specific primers. Preferably, the allele-specific primer contains a portion of wild-type sequence, more preferably at least about 3-40 consecutive nucleotides of wild-type sequence.

In one embodiment, detection of a variant nucleic acid is performed using an RT-PCR assay, such as the TaqMan® assay, which is also known as the 5' nuclease assay (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, *PCR Method Appl.*, 4:357-362; Tyagi et al, 1996, *Nature Biotechnology*, 14:303-308; Nazarenko et al., 1997, *Nucl. Acids Res.*, 25:2516-2521; U.S. Pat. Nos. 5,866,336 and 6,117,635). The TaqMan® assay detects the accumulation of a specific amplified product during PCR. The TaqMan® assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye can be at the 5' most and the 3' most ends, respectively or vice versa. Alternatively, the reporter dye can be at the 5' or 3' most end while the quencher dye is attached to an internal nucleotide, or vice versa. In yet another embodiment, both the reporter and the quencher can be attached to internal nucleotides at a distance from each other such that fluorescence of the reporter is reduced.

During PCR, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The DNA polymerase cleaves the probe between the reporter dye and the quencher dye only if the probe hybridizes to the target mutation-containing template which is amplified during PCR, and the probe is designed to hybridize to the target mutation site only if a particular mutation allele (e.g., SNP, insertion or deletion) is present.

TaqMan® primer and probe sequences can readily be determined using the variant and associated nucleic acid sequence information provided herein. A number of computer programs, such as Primer Express (Applied Biosystems, Foster City, Calif.), can be used to rapidly obtain optimal primer/probe sets. It will be apparent to one of skill in the art that such primers and probes for detecting the variants of the present invention are useful in diagnostic assays for myeloproliferative disorders and related pathologies, and can be readily incorporated into a kit format. The present invention also includes modifications of the TaqMan® assay well-known in the art such as the use of Molecular Beacon probes (U.S. Pat. Nos. 5,118,801 and 5,312,728) and other variant formats (U.S. Pat. Nos. 5,866,336 and 6,117,635).

In an illustrative embodiment, real time PCR is performed using TaqMan® probes in combination with a suitable amplification/analyzer such as the ABI Prism® 7900HT Sequence Detection System. The ABI PRISM® 7900HT Sequence Detection System is a high-throughput real-time PCR system that detects and quantitates nucleic acid sequences. Briefly, TaqMan® probes specific for the amplified target or marker sequence are included in the PCR amplification reaction. These probes contain a reporter dye at the 5' end and a quencher dye at the 3' end. Probes hybridizing to different target or marker sequences are conjugated with a different fluorescent reporter dye. During PCR, the fluorescently labeled probes bind specifically to their respective target or marker sequences; the 5' nuclease activity of Taq polymerase cleaves the reporter dye from the probe and a fluorescent signal is generated. The increase in fluorescence signal is detected only if the target or marker sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation. Real time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

Other methods of probe hybridization detected in real time can be used for detecting amplification a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Amplified fragments can be detected using standard gel electrophoresis methods. For example, in preferred embodiments, amplified fractions are separated on an agarose gel and stained with ethidium bromide by methods known in the art to detect amplified fragments.

In some embodiments, amplified nucleic acids are detected by hybridization with a mutation-specific probe. Probe oligonucleotides, complementary to a portion of the amplified target sequence can be used to detect amplified fragments. Amplified nucleic acids for each of the target sequences can be detected simultaneously (i.e., in the same reaction vessel) or individually (i.e., in separate reaction vessels). In some embodiments, the amplified DNA is detected simultaneously, using two distinguishably-labeled, gene-specific oligonucleotide probes, one which hybridizes to the first target sequence and one which hybridizes to the second target sequence. Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe can be labeled.

Another suitable detection methodology involves the design and use of bipartite primer/probe combinations such as Scorpion™ probes. These probes perform sequence-specific priming and PCR product detection is achieved using a single molecule. Scorpion™ probes comprise a 3' primer with a 5' extended probe tail comprising a hairpin structure which possesses a fluorophore/quencher pair. The probe tail is "protected" from replication in the 5' to 3' direction by the inclusion of hexethlyene glycol (HEG) which blocks the polymerase from replicating the probe. The fluorophore is attached to the 5' end and is quenched by a moiety coupled to the 3' end. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product. Such probes are described in Whitcombe et al., *Nature Biotech* 17: 804-807 (1999).

In some embodiments, two or more assays are performed for detection of any of the variants described herein. In some embodiments, the identity of any of the variants described herein is confirmed by nucleic acid sequencing.

Isolation of CALR Proteins

CALR proteins with and without deletions mutations (e.g. a p.E381_A382>A deletion, a p.D397_D400>D deletion, and a p.E405_V409>V deletion) and/or other mutations described herein can be recovered from biological sample from an individual, culture medium or from host cell lysates. If membrane-bound, it can be released from the membrane using a suitable detergent solution (e.g., Triton-X 100) or by enzymatic cleavage. Cells employed in the expression of CALR protein can be disrupted by various physical or chemical means, such as freeze-thaw cycling, sonication, mechanical disruption, or cell lysing agents.

In some embodiments, the coding sequence for the mutant or wild-type CALR protein is expressed in a mammalian cell through the use of a mammalian expression system, either inducible or constitutively, following introduction of the mammalian expression system along with the coding sequences of interest into the mammalian cell. Examples of mammalian cells include, but are not limited to, COS-7 cell, HEK-293 cell, U20S cell, and HeLa.

It can be desired to purify CALR protein from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the CALR. Various methods of protein purification can be employed and such methods are known in the art and described for example in Deutscher, Methods in Enzymology (1990), 182:83-89; Scopes, Protein Purification: Principles and Practice, Springer-Verlag, New York (1982). The purification step(s) selected will depend, for example, on the nature of the production process, source of CALR used and the particular CALR produced.

Detection of CALR Proteins

Several methods for detection of proteins are well-known in the art. Detection of the proteins can involve resolution of the proteins by SDS polyacrylamide gel electrophoresis (SDS PAGE), followed by staining the proteins with suitable stain, for example, Coomassie Blue. The CALR proteins with and without a mutation can be differentiated from each other and also from other proteins by Western blot analysis using mutation-specific antibodies. Methods for performing a Western blot are well-known in the art and described, for example, in W. Burnette W. N. *Anal. Biochem.* 1981; 112 (2): 195-203.

Alternatively, flow cytometry can be applied to detect the mutant and wild-type CALR protein. Antibodies specific for either the mutant or wild-type protein can be coupled to beads and can be used in the flow cytometry analysis.

In some embodiments, protein microarrays can be applied to identify the various CALR protein variants. Methods of protein arrays are well-known in the art. In one example, antibodies specific for each protein can be immobilized on the solid surface such as glass or nylon membrane. The proteins can then be immobilized on the solid surface through the binding of the specific antibodies. Antibodies can be applied that bind specifically to a second epitope (e.g., an epitope common to the mutant and wild-type) of the CALR proteins. The first antibody/protein/second antibody complex can then be detected using a detectably labeled secondary antibody. The detectable label can be detected as provided herein for polynucleotides and as is known in the art.

In some embodiments, recombinant CALR proteins can be engineered to contain the deletion mutation. In some embodiments, the recombinant CALR proteins contain an epitope tag (e.g. a peptide tag, such as a myc or HA tag). In some embodiments, the epitope tag can be removed from the protein after expression and/or purification of the recombinant protein.

Antibody Production and Screening

Various procedures known in the art can be used for the production of antibodies to epitopes of the CALR protein that can be used to distinguish among the protein variants. Such antibodies include but are not limited to polyclonal, monoclonal, chimeric, single chain, Fab fragments and fragments produced by a Fab expression library.

Antibodies can be radioactively labeled allowing one to follow their location and distribution in the body after injection. Radioactivity tagged antibodies can be used as a non-invasive diagnostic tool for imaging de novo cells of tumors and metastases.

Immunotoxins can also be designed which target cytotoxic agents to specific sites in the body. For example, high affinity CALR-specific monoclonal antibodies can be covalently complexed to bacterial or plant toxins, such as diphtheria toxin, abrin or ricin. A general method of preparation of antibody/hybrid molecules can involve use of thiol-crosslinking reagents such as SPDP, which attack the primary amino groups on the antibody and by disulfide exchange, attach the toxin to the antibody. The hybrid antibodies can be used to specifically eliminate mutant CALR protein-expressing cells.

For the production of antibodies, various host animals can be immunized by injection with the full length or fragment of CALR proteins including but not limited to rabbits, mice, rats, etc. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to CALR proteins can be prepared by using any technique which provides for the production of antibody molecules by continuous cell lines in culture. These include, but are not limited to, the hybridoma technique originally described by Kohler and Milstein, (*Nature* (1975), 256:495-497), the human B-cell hybridoma technique (Kosbor et al., *Immunology Today* (1983), 4:72; Cote et al. *Proc. Natl. Acad. Sci.* (1983), 80:2026-2030) and the EBV-hybridoma technique (Cole et al., Monoclonal Antibodies and Cancer Therapy (1985), Alan R. Liss, Inc., pp. 77-96). In addition, techniques developed for the production of "chimeric antibodies" by splicing the genes from a mouse antibody molecule of appropriate antigen specificity together with genes from a human antibody molecule of appropriate biological activity can be used (Morrison et al., *Proc. Natl. Acad. Sci. USA* (1984), 81:6851-6855; Neuberger et al., *Nature* (1984), 312:604-608; Takeda et al., *Nature* (1985), 314:452-454). Alternatively, techniques described for the production of single chain antibodies (U.S. Pat. No. 4,946,778) can be adapted to produce CALR protein-specific single chain antibodies.

Antibody fragments can be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., *Science*, 1989; 246: 1275-1281) to allow rapid and easy identification of monoclonal Fab fragments with the desired specificity.

Methods of Treatment

Methods of treating myeloproliferative disorders are also provided herein and can be used in combination with the diagnostic and prognostic method provided for detection and monitoring of the CALR mutations described (e.g. a p.E381_A382>A deletion, a p.D397_D400>D deletion, and a p.E405_V409>V deletion). In some embodiments, methods for detecting CALR mutations are provided for treating, diagnosing, providing prognosis, and/or managing a disease or condition related to a myeloproliferative disorder. In some embodiments, methods for detecting CALR mutations are provided for treating a cancer or disease or condition related to a CALR mutation, in conjunction with one or more therapies effective in treating the cancer or disease, including but not limited to drug therapy (e.g. a chemotherapeutic drug), radiation treatment (e.g. x-ray, γ-ray, or electron, proton, neutron, or a particle beam), hyperthermia heating (e.g. microwave, ultrasound, radiofrequency ablation), vaccine therapy, gene therapy, photodynamic therapy, surgery, and bone marrow or stem cell transplantation.

Exemplary treatments for myeloproliferative neoplasms include, but are not limited to, phlebotomy, platelet apheresis, transfusion therapy, chemotherapy, radiation therapy (e.g. external or internal radiation therapy with radioactive substances), other drug therapy (e.g. prednisone, danazol, anagrelide, low-dose aspirin, thalidomide, lenalidomide, and pomolidomide), surgery (e.g. splenectomy), biologic therapy (e.g. immunotherapeutic agents, such as interferon alfa, pegylated interferon alpha, and erythropoietic growth factors), targeted therapy (e.g. tyrosine kinase inhibitors such as ruxolotinib), high-dose chemotherapy with stem cell transplant.

In some embodiments, methods for detecting and identifying CALR mutations are provided for treating CALR mutations related to a disease or condition or cancer, for example, a myeloproliferative neoplasm, in a subject by administering to the subject an effective amount of a composition including one or more suitable chemotherapeutic agents. In some embodiments, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. Chemotherapeutic agents commonly used for the treatment of myeloproliferative neoplasms include, but are not limited to, arsenic trioxide, azacitidine, cyclophosphamide, cytarabine, dasatinib, daunorubicin hydrochloride, decitabine, doxorubicin hydrochloride, imatinib mesylate, nilotinib, ruxolitinib phosphate, and vincristine sulfate.

Routes and frequency of administration of the therapeutic agents disclosed herein, as well as dosage, will vary from individual to individual as well as with the selected drug, and can be readily established using standard techniques. In general, the pharmaceutical compositions can be administered, by injection (e.g., intracutaneous, intratumoral, intramuscular, intravenous or subcutaneous), intranasally (e.g., by aspiration) or orally. In a particular embodiment, the pharmaceutical composition is administered orally. In one example, between 1 and 10 doses can be administered over a 52 week period. Preferably, 6 doses are administered, at intervals of 1 month, and booster treatments can be given periodically thereafter. Alternate protocols can be appropriate for individual patients. In one embodiment, 2 intradermal injections of the composition are administered 10 days apart.

A "solid oral dosage form," "oral dosage form," "unit dose form," "dosage form for oral administration," and the like are used interchangably, and refer to a pharmaceutical composition in the form of a tablet, capsule, caplet, gelcap, geltab, pill and the like.

Dosage forms typically include an "excipient," which as used herein, is any component of an dosage form that is not an API. Excipients include binders, lubricants, diluents, disintegrants, coatings, barrier layer components, glidants, and other components. Excipients are known in the art (see HANDBOOK OF PHARMACEUTICAL EXCIPIENTS, FIFTH EDITION, 2005, edited by Rowe et al., McGraw Hill). Some excipients serve multiple functions or are so-called high functionality excipients. For example, talc can act as a lubricant, and an anti-adherent, and a glidant. See Pifferi et al., 2005, "Quality and functionality of excipients" Farmaco. 54:1-14; and Zeleznik and Renak, Business Briefing: Pharmageneris 2004.

A suitable dose is an amount of a compound that, when administered as described above, is capable of promoting an anti-cancer therapeutic response, and is at least 10-50% above the basal (i.e., untreated) level. Such response can be monitored using conventional methods. In general, for pharmaceutical compositions, the amount of each drug present in a dose ranges from about 100 µg to 5 mg per kg of host, but those skilled in the art will appreciate that specific doses depend on the drug to be administered and are not necessarily limited to this general range. Likewise, suitable volumes for each administration will vary with the size of the patient.

In the context of treatment, a "therapeutically effective amount" of a drug is an amount of or its pharmaceutically acceptable salt which eliminates, alleviates, or provides relief of the symptoms for which it is administered. The disclosed compositions are administered in any suitable manner, often with pharmaceutically acceptable carriers. Suitable methods of administering treatment in the context of the present invention to a subject are available, and, although more than one route can be used to administer a particular composition, a particular route can often provide a more immediate and more effective reaction than another route. The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose."

In general, an appropriate dosage and treatment regimen involves administration of the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

Kits

The present inventions also contemplate diagnostic systems in kit form. In some embodiments, a kit can be used for conducting the diagnostic, prognostic, or treatment methods described herein. In some embodiments, a kit can be used as a companion diagnostic for detection of a CALR exon 9 indel mutation in a subject has received one or more treatments for a CALR-related disease or condition or a JAK2-related disease or condition. In some embodiments, the CALR-related disease or condition or a JAK2-related disease or condition is a myeloproliferative disease, such as polycythemia vera, essential thrombocythemia, idiopathic myelofibrosis, and unclassified myeloproliferative disease. Typically, the kit should contain, in a carrier or compartmentalized container, reagents useful in any of the above-described embodiments of the methods.

A diagnostic system provided herein can include a kit which contains, in an amount sufficient for at least one assay, any of the hybridization assay probes and amplification primers for detection of CALR wild type and mutant nucleic acids, and/or antibodies against CALR wild type and mutant proteins in a packaging material. In some embodiments the kit further comprises reagents for the detection of additional mutations in one or more genes involved in myeloproliferative disease, such as, for example, a gene encoding a JAK-STAT pathway protein.

In some embodiments, the kit includes one or more primers or probes suitable for amplification and/or sequencing. Exemplary primers include primers of selected from SEQ ID NOs: 10-13. The primers can be labeled with a detectable marker such as radioactive isotopes, or fluorescence markers.

Typically, the kits will also include instructions recorded in a tangible form (e.g., contained on paper or an electronic medium) for using the packaged probes, primers, and/or antibodies in a detection assay for determining the presence or amount of mutant nucleic acid or protein in a test sample.

The various components of the diagnostic systems can be provided in a variety of forms. For example, the required enzymes, the nucleotide triphosphates, the probes, primers, and/or antibodies can be provided as a lyophilized reagent. These lyophilized reagents can be pre-mixed before lyophilization so that when reconstituted they form a complete mixture with the proper ratio of each of the components ready for use in the assay. In addition, the diagnostic systems of the present inventions can contain a reconstitution reagent for reconstituting the lyophilized reagents of the kit. In preferred kits, the enzymes, nucleotide triphosphates and required cofactors for the enzymes are provided as a single lyophilized reagent that, when reconstituted, forms a proper reagent for use in the present amplification methods.

In some embodiments, the kit includes suitable buffers, reagents for isolating nucleic acid, and instructions for use. Kits can also include a microarray that contains nucleic acid or peptide probes for the detection of the mutant genes or encoded proteins, respectively.

In some embodiments, the kits can further contain a solid support for anchoring the nucleic acid or proteins of interest on the solid support. In some embodiments, the target nucleic acid can be anchored to the solid support directly or indirectly through a capture probe anchored to the solid support and capable of hybridizing to the nucleic acid of interest. Examples of such solid supports include, but are not limited to, beads, microparticles (for example, gold and other nanoparticles), microarray, microwells, multiwell plates. The solid surfaces can comprise a first member of a binding pair and the capture probe or the target nucleic acid can comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, antigen/antibody.

Exemplary packaging for the kit can include, for example, a container or support, in the form of, e.g., bag, box, tube, rack, and is optionally compartmentalized. The packaging can define an enclosed confinement for safety purposes during shipment and storage.

The following examples serve to illustrate the present invention. These examples are in no way intended to limit the scope of the invention.

EXAMPLES

Example 1

Identification of CALR Exon 9 In-frame Deletions

We determined the frequency of CALR exon 9 in-frame protein alterations in samples submitted for rule out/suspicion of a myeloproliferative neoplasm (RO MPN). We also assessed whether in-frame CALR alterations are differentially associated with +1 bp CALR frameshift mutations or with JAK2 V617F or other somatic mutations in MPN-associated genes.

CALR mutations were assessed in 1394 JAK2 V617F-negative blood (n=1253) and bone marrow (n=141) samples initially submitted for RO MPN. An additional set of 94 JAK2 V671F-positive samples was also tested for CALR mutations.

Mutation analysis of CALR exon 9 was performed on genomic DNA extracted from the samples of blood, bone marrow aspirate, or fixed bone marrow biopsy sections using a Sanger sequencing assay with an analytic sensitivity of at least 15% (minimum detection limit). A subset of cases was further assessed with mutation quantification using an Ion Torrent sequencing panel to assess exon 9 of CALR, exon 14 and exon 17 of CSF3R, exon 12 or exon 14 of JAK2, and exon 10 MPL; a second panel assessing ASXL1 (Additional Sex Combs Like 1), EZH2 (enhancer of zeste homolog 2), IDH1 (isocitrate dehydrogenase 1), IDH2 (isocitrate dehydrogenase 2), KRAS (Kirsten rat sarcoma viral oncogene homolog), NRAS (neuroblastoma RAS viral (v-ras) oncogene homolog), and TET2 (tet methylcytosine dioxygenase 2); or an Illumina TruSeq extended panel assessing these genes and additional 18 MPN-associated genes (i.e., ASXL1, CALR, CBL, CEBPA, CSF3R, DDX41, DNMT3A, EZH2, FLT3, GATA1, IDH1, IDH2, JAK2, KDM6A, KIT, KRAS, MPL, NPM1, NRAS, PTPN11, RUNX1, SETBP1, SF3B1, SRSF2, TET2, TP53, U2AF 1, WT1 and ZRSR2). One sizing assay was also performed (MLL PTD sizing assay). The 29 genes and the corresponding exons assayed by MiSeq sequencing (417 amplicons) are listed in Table 1. This sequencing panel includes nearly all of the currently known important prognostic mutation markers (or differentially mutated genes) in AML, MDS and MPN/MDS. These assays had a sensitivity of approximately 5%. JAK2 V617F mutations were quantitated using a pyrosequencing assay with an analytic sensitivity of 1%.

TABLE 1

Exons for each gene and partial or full exons are covered in the panel

| Gene Symbol | Targeted Region | Total number of Exons |
|---|---|---|
| ASXL1 | Exon 13 | 1 |
| CALR | Exon 9 | 1 |
| CBL | Exons 1-16 | 16 |
| CEBPA | Exon 1 | 1 |
| CSF3R | Exons 3 to 13, and 17 | 12 |
| DDX41 | Exon 14, 15 | 2 |
| DNMT3A | all encoding exons | 22 |
| EZH2 | all encoding exons | 19 |
| FLT3 | Exons 11, 12, 14, 15, 16,20 | 6 |
| GATA1 | all encoding exons | 5 |
| IDH1 | Exon 4 | 1 |
| IDH2 | Exon 4 | 1 |
| JAK2 | Exon 12, 13, 14 | 3 |
| KDM6A | all encoding exons | 29 |
| KIT | Exon 8, 9, 10, 11, 17 | 5 |
| KRAS | all encoding exons | 5 |
| MLL | Exons 2-8 | 7 (dup analysis only) |
| MPL | all encoding exons | 12 |
| NPM1 | Exon 12 | 1 |
| NRAS | all encoding exons | 4 |
| PTPN11 | all encoding exons | 14 |
| RUNX1 | all encoding exons | 8 |
| SETBP1 | Exons 2, 3, 4, 5, 6 | 5 |
| SF3B1 | Exons 11-18 | 8 |
| SRSF2 | all encoding exons | 2 |
| TET2 | all encoding exons | 9 |
| TP53 | ALL CDS | 10 |
| U2AF1 | all encoding exons | 8 |
| WT1 | all encoding exons | 10 |
| ZRSR2 | ALL CDS | 11 |
| | Total number of exons | 228 |
| | Total number of amplicons | 417 |

Illumina MiSeq sequencing employs a reversible fluorescent dye terminator-based method to sequence millions of DNA molecules in parallel by detecting the incorporation of single bases during DNA synthesis. The DNA library preparation is based on the Illumina TruSeq Custom Amplicon (TSCA) method that involves using a pool of DNA probes to specifically hybridize to the targeted regions then by probe extension and ligation to form double strand DNA which is sequentially amplified to sequence the DNA templates. The protocol involves the following steps: 1) DNA extraction; 2) DNA probe hybridization and clean-up; 3) PCR with index addition; 4) cluster generation and sequencing on the Illumina MiSeq system.

Briefly, DNA is extracted from whole blood, bone marrow aspirate, or fixed cell pellets. Oligonucleotide probes are pooled into a single Custom Amplicon Tube (CAT) containing all of the probes needed to hybridize to the targeted regions. The custom probes are added to each sample and hybridized to the specific targeted genomic regions by slowly decreasing temperature from 95° C. to 40° C. within 80 minutes followed by a purification step to remove any unbound probes. Next, an extension-ligation step is performed by the addition of DNA polymerase and DNA ligase to generate double strand DNA fragments which are flanked by common sequences needed for PCR amplification. Sample-specific multiplexing index sequences are then added to each library by PCR using common sequences included in the probes and index PCR primers. The PCR product is then purified and quantified using real-time PCR. Up to 24 uniquely indexed individual libraries are mixed equally, denatured and diluted to make a pooled library at a concentration of 20 pM. This pooled library is further heat-denatured before being added to the MiSeq reagent cartridge which then is loaded onto the MiSeq for sequencing. An overview of the sequencing methods if provided in FIG. 1.

The sequencing data is base-called using Illumina Basecaller software, aligned using SeqNext software (JSI Medical Systems) or GATK/BWA software using GRCh37/hg19 as the reference sequence and mutations are called and annotated by SeqNext or Alamut software (see CHA MO.061). This qualitative test reports as "POSITIVE" or "NEGATIVE" for mutation(s) in the 29 genes on the sequencing panel as well as the MLL PTD sizing assay. It can be used for detecting the range of mutations present in a myeloid or related neoplasm at diagnosis and for monitoring the relapse or therapy response of patients by comparison with mutation read level in the initial sample. Exemplary primers employed for CALR variant detection are shown in Table 2 below.

Figure 2:
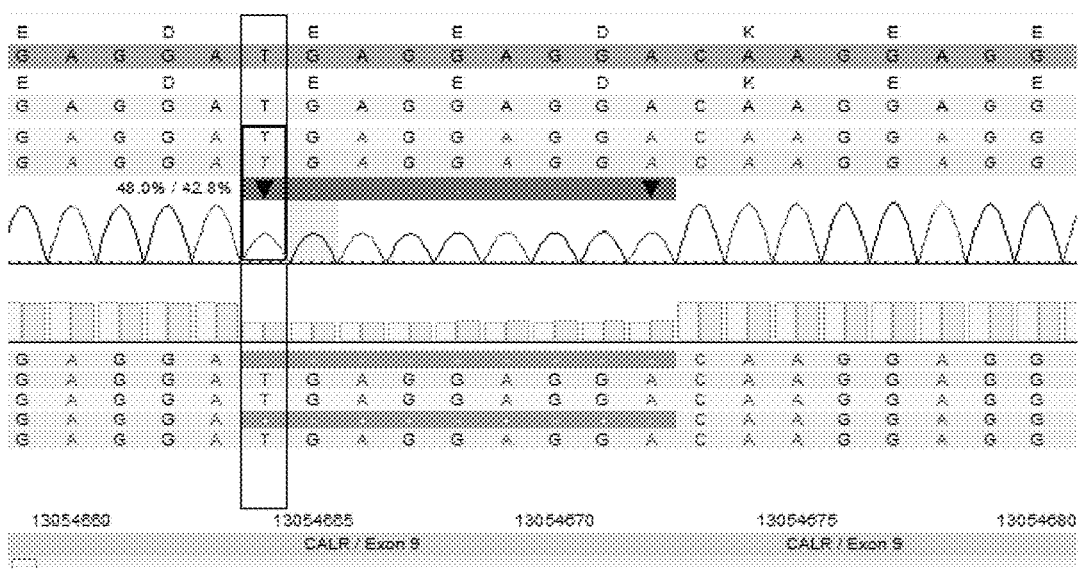
FIG. 2 illustrates (A) a representative sequence of an exemplary exon 9 CALR in-frame deletion (indel) producing a C-terminal modified protein (p.D397_D400>D) (SEQ ID NOS 19, 18, 19, 18, 18, 20, 18, 18, 20 and 18, respectively, in order of appearance) and (B) a representative alignment of C-terminal of wild-type CALR proteins from various species (SEQ ID NOS 21-26, respectively, in order of appearance). Reference sequences are derived from NP_004334 (*H. sapiens*) (SEQ ID No: 2), XP_003316194 (*P. troglodytes*) (SEQ ID No: 4), NP_001248060 (*M. mulatta*) (SEQ ID No: 5), XP_867310.2 (*C. lupus*) (SEQ ID No: 6), NP_031617.1(*M. musculus*) (SEQ ID No: 8), and NP_071794.1 (*R. norvegicus*) (SEQ ID No: 9). The most common in-frame deletion is conserved (underlined).
Figure 3:
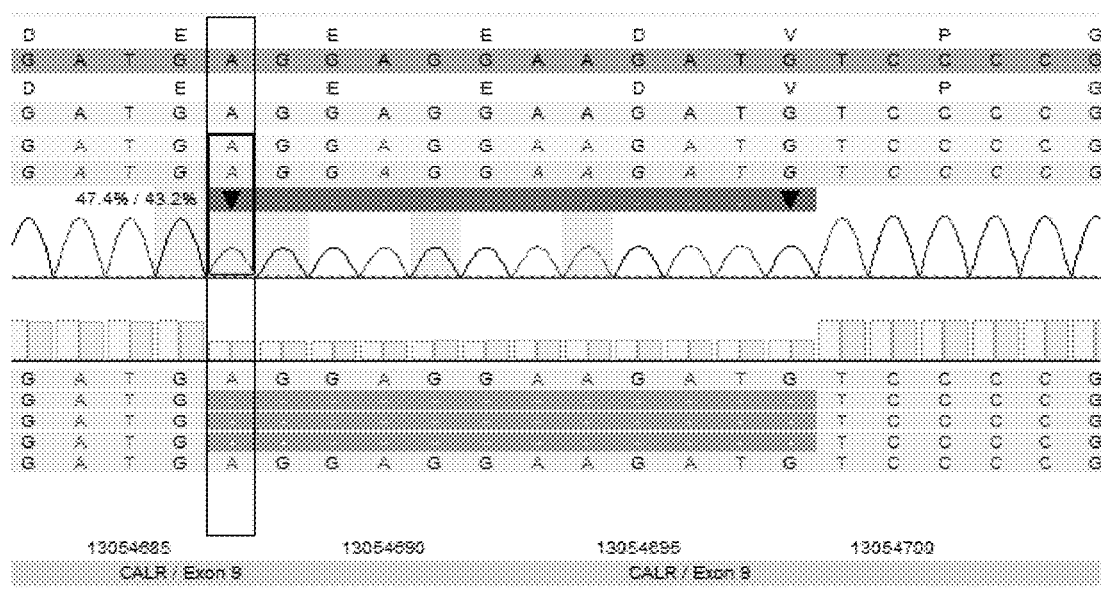
FIG. 3 illustrates (A) a representative sequence of an exemplary exon 9 CALR in-frame deletion (indel) producing a C-terminal modified protein (p.E405_V409>V) (SEQ ID NOS 28, 27, 28, 27, 27, 27, 27, 29, 29, 29 and 27, respectively, in order of appearance).
Figure 4:
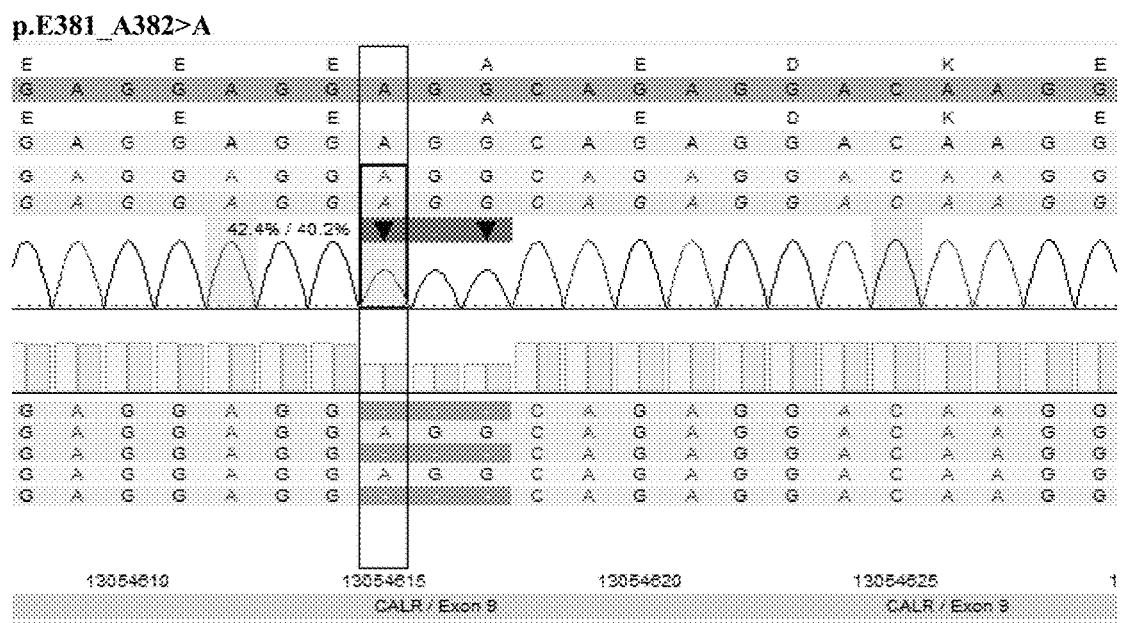
FIG. 4 illustrates (A) a representative sequence of an exemplary exon 9 CALR in-frame deletion (indel) producing a C-terminal modified protein (p.E381_A382>A) (SEQ ID NOS 31, 30, 31, 30, 30, 30, 32, 30, 32, 30 and 32, respectively, in order of appearance).
Figure 5:
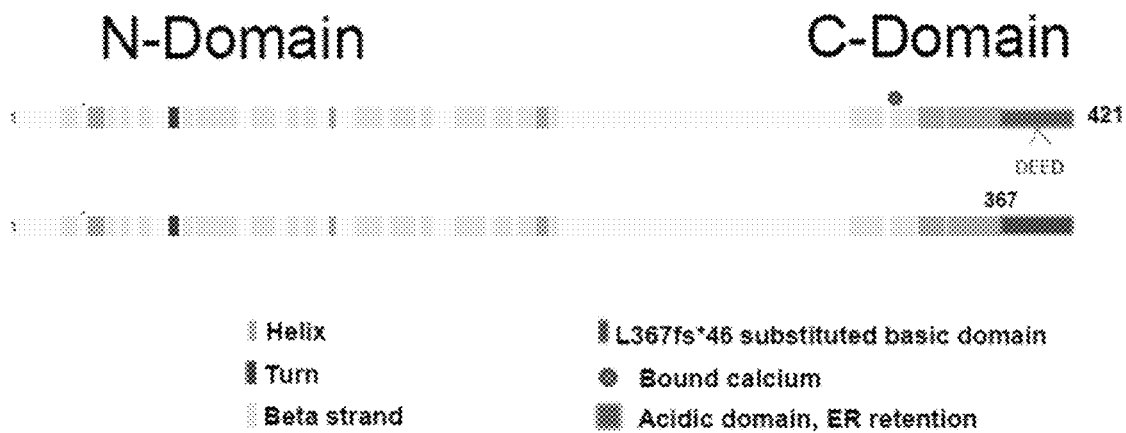
FIG. 5 illustrates the structural domains of the CALR protein, with areas affected by frameshift mutations and the most common in-frame C-terminal size polymorphism highlighted. The N-domain and C-domain are the main sites for binding of interacting proteins during endoplasmic reticulum trafficking ("DEED" disclosed as SEQ ID NO: 15). The p.L367fs*46+1-bp mutation in ET/PMF results in shift of the C-terminal sequences from a predominance of acidic to basic amino acids and loss of the ER-retention KDEL motif (SEQ ID NO: 14).

(type 1), 71 with K385fs*47 and 43 with other +1 frameshifts involving codons 367-379, 373-374 and 384-385. Two cases (0.1%) had point mutations (E381A and D373N). Nine cases (0.6%) had in-frame deletions, including p.D397_D400>D (n=6, FIG. 2), p.E381_A382>A (n=2), and p.E405_V409>V (n=1). All E9 in-frame deletions were present in approximately 50% of reads, suggesting a germline polymorphism (Table 3). Clinical diagnoses in these in-frame indels were cytopenia/BM fibrosis, ET, thrombocytosis/anemia, and RO MPN unspecified.

TABLE 3

In-frame CALR exon 9 indel sequence alterations

| Predicted change in CALR protein | Read level (%) | Additional mutations in 28 additional MPN-associated genes |
|---|---|---|
| p.E381_A3820>A | 52% | None |
| p.E381_A382>A | 41% | MPL W515L (40%, COSM18918) CSF3R A470T (46%, COSM186717) |
| p.D397_D400>D | 45% | MPL D163Y (12%) |
| p.D397_D400>D | 49% | JAK2 V617F (28%, COSM12600) |
| p.D397_D400>D | 49% | None |
| p.D397_D400>D | 48% | ASXL1 D954fs*26 (45%) |
| p.D397_D400>D | 48% | None |
| p.D397_D400>D | 47% | None |
| p.D397_D400>D | 47% | None |
| p.E405_V409>V | 45% | ZRSR2 S449_R450dup (27%, c.1338_1343dupGAGCCG) |

In a parallel set of 94 JAK2 V617F-positive MPN samples, CALR mutations in only 2 samples was noted: the p.D397_D400>D in-frame deletion was detected in one ET case with 28% JAK2 V617F mutation, and a K385fs*47 CALR mutation was detected at heterozygous levels in one case with low-level (4.2%) JAK2 V617F. Among 185 cases with a referring diagnosis of acute myeloid leukemia (AML) or myelodysplastic syndrome (MDS), the p.D397_D400>D in-frame deletion was noted in one pancytopenia case.

The C-terminal region of calreticulin functions in calcium-binding, with a shift in the isoelectric point (pI) from wild-type to mutant proteins seen in MPN likely influencing the degree of calcium binding (Shivarov et al. *Blood Cancer Journal* 2014 4:e185). The CALR gene is highly conserved, with its unstructured acidic C-terminal sequence identical in many species. However, the consensus chimpanzee (*P. troglodytes*) sequence shows a similar deletion of acidic residues involving codons 493-497 compared to the other proteins (FIG. 2B). The loss of some acidic residues in the variants

TABLE 2

| Target ID | Chr. # | Start Position | End Position | Upstream Primer Sequence | Downstream Primer Sequence |
|---|---|---|---|---|---|
| CALR.1.line.25.chr19. 13054525.13054728_tile_1 | chr19 | 13054525 | 13054728 | AGGAGCGCTCAGGC CTCAGTCCAGCC (SEQ ID NO: 10) | CAGGCAGAGCACACACCT CAGG (SEQ ID NO: 11) |
| CALR.1.line.25.chr19. 13054525.13054728_tile_2 | chr19 | 13054525 | 13054728 | AGCTGTAGAGAGGC CTGCCTCCA (SEQ ID NO: 12) | TATCTTTGATTCTCCTTCA GCCCTCAC (SEQ ID NO: 13) |

CALR exon 9 mutation status was assessed in 1394 samples submitted for RO MPN that were negative for JAK2 V617F mutation. Of these, 264 (18.9%) had typical +1 frameshift mutations, including 150 with L367fs*46 above would shift the pI, possibly affecting chaperone function (Villamil et al. *J Biol Chem* 201 Feb. 12; 285(7): 4544-53; Jorgensen et al. *Protein Pept Lett* 2005 October; 12(7):687-93

To assess the other features of the samples containing these variants, we tested for mutations in 28 additional MPN-associated genes (Table 1). Definitive somatic mutations were detected in 5 (50%) of the 10 in-frame CALR indel cases, including MPL (W515L, 40%; D163Y,12%), CSF3R (A470T 46%), ASXL1 (D954fs*26, 45%), and ZRSR2 (S449_R450dup, 27%). The frequency of mutations in CSF3R and MPL was higher than in RO MPN samples of all types.

In summary, it was found that CALR exon 9 in-frame deletions occurred in 0.6% of samples submitted for workup of myeloid neoplasms and were always present at heterozygous levels, favoring classification as normal sequence variants. It was also found that 50% of these variants had an additional mutation in another MPN-associated gene. The p.D397_D400>D in-frame deletion was the most common change, but other in-frame deletions involving the C-terminal acidic region were observed. These relatively common size polymorphisms in CALR indicate that sizing assays for diagnosis of pathogenic +1 frameshift mutations can need to be complemented by definitive DNA sequencing to identify the deletion mutations. RO MPN samples with CALR in-frame deletions can be associated with a higher frequency of pathogenic JAK-STAT pathway mutations.

It should be understood that although the present invention has been specifically disclosed by preferred embodiments and optional features, modification, improvement and variation of the inventions embodied therein herein disclosed can be resorted to by those skilled in the art, and that such modifications, improvements and variations are considered to be within the scope of this invention. The materials, methods, and examples provided here are representative of particular embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein can suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Additional embodiments are set forth within the following claims.

SEQUENCE LISTING

>SEQ ID NO: 1
>CALR nucleotide coding sequence
ATGCTGCTATCCGTGCCGCTGCTGCTCGGCCTCCTCGGCCTGGCCGTCGC

CGAGCCTGCCGTCTACTTCAAGGAGCAGTTTCTGGACGGAGACGGGTGGA

CTTCCCGCTGGATCGAATCCAAACACAAGTCAGATTTTGGCAAATTCGTT

CTCAGTTCCGGCAAGTTCTACGGTGACGAGGAGAAAGATAAAGGTTTGCA

GACAAGCCAGGATGCACGCTTTTATGCTCTGTCGGCCAGTTTCGAGCCTT

TCAGCAACAAAGGCCAGACGCTGGTGGTGCAGTTCACGGTGAAACATGAG

CAGAACATCGACTGTGGGGGCGGCTATGTGAAGCTGTTTCCTAATAGTTT

GGACCAGACAGACATGCACGGAGACTCAGAATACAACATCATGTTTGGTC

CCGACATCTGTGGCCCTGGCACCAAGAAGGTTCATGTCATCTTCAACTAC

AAGGGCAAGAACGTGCTGATCAACAAGGACATCCGTTGCAAGGATGATGA

GTTTACACACCTGTACACACTGATTGTGCGGCCAGACAACACCTATGAGG

TGAAGATTGACAACAGCCAGGTGGAGTCCGGCTCCTTGGAAGACGATTGG

GACTTCCTGCCACCCAAGAAGATAAAGGATCCTGATGCTTCAAAACCGGA

AGACTGGGATGAGCGGGCCAAGATCGATGATCCCACAGACTCCAAGCCTG

AGGACTGGGACAAGCCCGAGCATATCCCTGACCCTGATGCTAAGAAGCCC

GAGGACTGGGATGAAGAGATGGACGGAGAGTGGGAACCCCCAGTGATTCA

GAACCCTGAGTACAAGGGTGAGTGGAAGCCCCGGCAGATCGACAACCCAG

ATTACAAGGGCACTTGGATCCACCCAGAAATTGACAACCCCGAGTATTCT

CCCGATCCCAGTATCTATGCCTATGATAACTTTGGCGTGCTGGGCCTGGA

CCTCTGGCAGGTCAAGTCTGGCACCATCTTTGACAACTTCCTCATCACCA

ACGATGAGGCATACGCTGAGGAGTTTGGCAACGAGACGTGGGGCGTAACA

AAGGCAGCAGAGAAACAAATGAAGGACAAACAGGACGAGGAGCAGAGGCT

TAAGGAGGAGGAAGAAGACAAGAAACGCAAAGAGGAGGAGGAGGCAGAGG

ACAAGGAGGATGATGAGGACAAAGATGAGGATGAGGAGGATGAGGAGGAC

AAGGAGGAAGATGAGGAGGAAGATGTCCCCGGCCAGGCCAAGGACGAGCT

G

>SEQ ID NO: 2
>gi|4757900|ref|NP_004334.1|calreticulin
precursor [Homo sapiens]
MLLSVPLLLGLLGLAVAEPAVYFKEQFLDGDGWTSRWIESKHKSDFGKFV

LSSGKFYGDEEKDKGLQTSQDARFYALSASFEPFSNKGQTLVVQFTVKHE

QNIDCGGGYVKLFPNSLDQTDMHGDSEYNIMFGPDICGPGTKKVHVIFNY

KGKNVLINKDIRCKDDEFTHLYTLIVRPDNTYEVKIDNSQVESGSLEDDW

DFLPPKKIKDPDASKPEDWDERAKIDDPTDSKPEDWDKPEHIPDPDAKKP

EDWDEEMDGEWEPPVIQNPEYKGEWKPRQIDNPDYKGTWIHPEIDNPEYS

PDPSIYAYDNFGVLGLDLWQVKSGTIFDNFLITNDEAYAEEFGNETWGVT

KAAEKQMKDKQDEEQRLKEEEEDKKRKEEEEAEDKEDDEDKDEDEEDEED

KEEDEEEDVPGQAKDEL

>SEQ ID NO: 3
>gi|209862753|ref|NM_004343.3|Homo sapiens
calreticulin (CALR), mRNA
GCGGCGTCCGTCCGTACTGCAGAGCCGCTGCCGGAGGGTCGTTTTAAAGG
GCCCGCGCGTTGCCGCCCCCTCGGCCCGCCATGCTGCTATCCGTGCCGCT
GCTGCTCGGCCTCCTCGGCCTGGCCGTCGCCGAGCCTGCCGTCTACTTCA
AGGAGCAGTTTCTGGACGGAGACGGGTGGACTTCCCGCTGGATCGAATCC
AAACACAAGTCAGATTTTGGCAAATTCGTTCTCAGTTCCGGCAAGTTCTA
CGGTGACGAGGAGAAAGATAAAGGTTTGCAGACAAGCCAGGATGCACGCT
TTTATGCTCTGTCGGCCAGTTTCGAGCCTTTCAGCAACAAAGGCCAGACG
CTGGTGGTGCAGTTCACGGTGAAACATGAGCAGAACATCGACTGTGGGGG
CGGCTATGTGAAGCTGTTTCCTAATAGTTTGGACCAGACAGACATGCACG
GAGACTCAGAATACCATCATGTTTGGTCCCGACATCTGTGGCCCTGGCAC
CAAGAAGGTTCATGTCATCTTCAACTACAAGGGCAAGAACGTGCTGATCA
ACAAGGACATCCGTTGCAAGGATGATGAGTTTACACACCTGTACACACTG
ATTGTGCGGCCAGACAACACCTATGAGGTGAAGATTGACAACAGCCAGGT
GGAGTCCGGCTCCTTGGAAGACGATTGGGACTTCCTGCCACCCAAGAAGA
TAAAGGATCCTGATGCTTCAAAACCGGAAGACTGGGATGAGCGGGCCAAG
ATCGATGATCCCACAGACTCCAAGCCTGAGGACTGGGACAAGCCCGAGCA
TATCCCTGACCCTGATGCTAAGAAGCCCGAGGACTGGGATGAAGAGATGG
ACGGAGAGTGGGAACCCCCAGTGATTCAGAACCCTGAGTACAAGGGTGAG
TGGAAGCCCCGGCAGATCGACAACCCAGATTACAAGGGCACTTGGATCCA
CCCAGAAATTGACAACCCCGAGTATTCTCCCGATCCCAGTATCTATGCCT
ATGATAACTTTGGCGTGCTGGGCCTGGACCTCTGGCAGGTCAAGTCTGGC
ACCATCTTTGACAACTTCCTCATCACCAACGATGAGGCATACGCTGAGGA
GTTTGGCAACGAGACGTGGGGCGTAACAAAGGCAGCAGAGAAACAAATGA
AGGACAAACAGGACGAGGAGCAGAGGCTTAAGGAGGAGGAAGAAGACAAG
AAACGCAAAGAGGAGGAGGAGGCAGAGGACAAGGAGGATGATGAGGACAA
AGATGAGGATGAGGAGGATGAGGAGGACAAGGAGGAAGATGAGGAGGAAG
ATGTCCCCGGCCAGGCCAAGGACGAGCTGTAGAGAGGCCTGCCTCCAGGC
TGGACTGAGGCCTGAGCGCTCCTGCCGCAGAGCTGGCCGCGCCAAATAA
TGTCTCTGTGAGACTCGAGAACTTTCATTTTTTTCCAGGCTGGTTCGGAT
TTGGGGTGGATTTTGGTTTTGTTCCCCTCCTCCACTCTCCCCCACCCCCT
CCCCGCCCTTTTTTTTTTTTTTTTAAACTGGTATTTTATCTTTGATTC
TCCTTCAGCCCTCACCCCTGGTTCTCATCTTTCTTGATCAACATCTTTC
TTGCCTCTGTCCCCTTCTCTCATCTCTTAGCTCCCCTCCAACCTGGGGGG
CAGTGGTGTGGAGAAGCCACAGGCCTGAGATTTCATCTGCTCTCCTTCCT
GGAGCCCAGAGGAGGGCAGCAGAAGGGGGTGGTGTCTCCAACCCCCCAGC
ACTGAGGAAGAACGGGCTCTTCTCATTTCACCCCTCCCTTTCTCCCCTG
CCCCCAGGACTGGGCCACTTCTGGGTGGGGCAGTGGGTCCCAGATTGGCT
CACACTGAGAATGTAAGAACTACAAACAAAATTTCTATTAAATTAAATTT
TGTGTCTCCAAAAAAAAAAAAAAAAAA >SEQ ID NO: 4
>gi|332853291|ref|XP_003316194.1|PREDICTED:
calreticulin [Pan troglodytes]
MLLSVPLLLGLLGLAVAEPAVYFKEQFLDGDWTSRWIESKHKSDFGKFV
LSSGKFYGDEEKDKGLQTSQDARFYALSASFEPFSNKGQTLVVQFTVKHE
QNIDCGGGYVKLFPNSLDQTDMHGDSEYNIMFGPDICGPGTKKVHVIFNY
KGKNVLINKDIRCKDDEFTHLYTLIVRPDNTYEVKIDNSQVESGSLEDDW
DFLPPKKIKDPDASKPEDWDERAKIDDPTDSKPEDWDKPEHIPDPAKKP
EDWDEEMDGEWEPPVIQNPEYKGEWKPRQIDNPDYKGTWIHPEIDNPEYS
PDPSIYAYDNEGVLGLDLWQVKSGTIFDNFLITNDEAYAEEFGNETWGVT
KAAEKQMKDKQDEEQRLKEEEEDKKRKEEEEAEDKEDDEDKDEDEEDKEE
DEEEDVPGQAKDEL >SEQ ID NO: 5
>gi|386780961|ref|NP_001248060.1|calreticulin
precursor [Macaca mulatta]
MLLSVPLLLGLLGLAAAEPAVYFKEQFLDGDWTSRWIESKHKSDFGKFV
LSSGKFYGDEEKDKGLQTSQDARFYALSASFEPFSNKGQTLVVQFTVKHE
QNIDCGGGYVKLFPNSLDQTDMHGDSEYNIMFGPDICGPGTKKVHVIFNY
KGKNVLINKDIRCKDDEFTHLYTLIVRPDNTYEVKIDNSQVESGSLEDDW
DFLPPKKIKDPDASKPEDWDERAKIDDPTDSKPEDWDKPEHIPDPAKKP
EDWDEEMDGEWEPPVIQNPEYKGEWKPRQIDNPDYKGTWIHPEIDNPEYS
PDPSIYAYDNFGVLGLDLWQVKSGTIFDNFLITNDEAYAEEFGNETWGVT
KAAEKQMKDKQDEEQRLKEEEEDKKRKEEEEAEDKEDDEDKDEDEEDEED
KEEDEEEDVPGQAKDEL >SEQ ID NO: 6
>gi|345787749|ref|XP_867310.2|PREDICTED:
calreticulin isoform 4 [Canis lupus familiaris]
MLLPVPLLLGLVGLAAAEPAIYFKEQFLDGDWTDRWIESKHKSDFGKFV
LSSGKFYNDQEKDKGLQTSQDARFYALSARFEPFSNKGQILVVQFTVKHE
QNIDCGGGYVKLFPDGLDQTDMHGDSEYNIMFGPDICGPGTKKVHVIFNY
KGKNVLINKDIRCKDDEFTHLYTLIVRPDNTYEVKIDNSQVESGSLEDDW
DFLPPKKIKDPDASKPEDWDERAKIDDPTDSKPEDWDKPEHIPDPAKKP
EDWDEEMDGEWEPPVIQNPEYKGEWKPRQIDNPDYKGTWIHPEIDNPEYS
PDSNIYAYENFAVLGLDLWQVKSGTIFDNFLITNDEAYAEEFGNETWGVT
KAAEKQMKDKQDEEQRLKEEEEDKKRKEEEEADKEDEEDKDEDEEDDDK
EEEEEEDDAAAGQAKDEL >SEQ ID NO: 7
>gi|27806723|ref|NP_776425.1|calreticulin
precursor [Bos taurus]
MLLPVPLLLGLLGLAAADPTVYFKEQFLDGDWTERWIESKHKPDFGKFV
LSSGKFYGDQEKDKGLQTSQDARFYALSARFEPFSNKGQILVVQFTVKHE
QNIDCGGGYVKLFPAGLDQTDMHGDSEYNIMFGPDICGPGTKKVHVIFNY
KGKNVLINKDIRCKDDEFTHLYTLIVRPNNTYEVKIDNSQVESGSLEDDW
DFLPPKKIKDPDAAKPEDWDDRAKIDDPTDSKPEDWDKPEHIPDPAKKP
EDWDEEMDGEWEPPVIQNPEYKGEWKPRQIDNPEYKGIWIHPEIDNPEYS
PDSNIYAYENFAVLGLDLWQVKSGTIFDNFLITNDEAYAEEFGNETWGVT
KAAEKQMKDKQDEEQRLHEEEEEKKGKEEEEADKDDDEDKDEDEEDEDEK

EEEEEEDAAAGQAKDEL

>SEQ ID NO: 8
>gi|6680836|ref|NP_031617.1|calreticulin
precursor [Mus musculus]
MLLSVPLLLGLLGLAAADPAIYFKEQFLDGDAWTNRWVESKHKSDFGKFV

LSSGKFYGDLEKDKGLQTSQDARFYALSAKFEPFSNKGQILVVQFTVKHE

QNIDCGGGYVKLFPSGLDQKDMHGDSEYNIMFGPDICGPGTKKVHVIFNY

KGKNVLINKDIRCKDDEFTHLYTLIVRPDNTYEVKIDNSQVESGSLEDDW

DFLPPKKIKDPDAAKPEDWDERAKIDDPTDSKPEDWDKPEHIPDPDAKKP

EDWDEEMDGEWEPPVIQNPEYKGEWKPRQIDNPDYKGTWIHPEIDNPEYS

PDANIYAYDSFAVLGLDLWQVKSGTIFDNFLITNDEAYAEEFGNETWGVT

KAAEKQMKDKQDEEQRLKEEEEDKKRKEEEEAEDKEDDDDRDEDEDEEDE

KEEDEEESPGQAKDEL

>SEQ ID NO: 9
>gi|11693172|ref|NP_071794.1|calreticulin
precursor [Rattus norvegicus]
MLLSVPLLLGLLGLAAADPAIYFKEQFLDGDAWTNRWVESKHKSDFGKFV

LSSGKFYGDQEKDKGLQTSQDARFYALSARFEPFSNKGQILVVQFTVKHE

QNIDCGGGYVKLFPGGLDQKDMHGDSEYNIMFGPDICGPGTKKVHVIFNY

KGKNVLINKDIRCKDDEFTHLYTLIVRPDNTYEVKIDNSQVESGSLEDDW

DFLPPKKIKDPDAAKPEDWDERAKIDDPTDSKPEDWDKPEHIPDPDAKKP

EDWDEEMDGEWEPPVIQNPEYKGEWKPRQIDNPDYKGTWIHPEIDNPEYS

PDANIYAYDSFAVLGLDLWQVKSGTIFDNFLITNDEAYAEEFGNETWGVT

KAAEKQMKDKQDEEQRLKEEEEDKKRKEEEEAEDKEDEDDRDEDEDEEDE

KEEDEEDATGQAKDEL

>SEQ ID NO: 10
>Synthetic nucleotide primer or probe
AGGAGCGCTCAGGCCTCAGTCCAGCC

>SEQ ID NO: 11
>Synthetic nucleotide primer or probe
CAGGCAGAGACACACACCTCAGG

>SEQ ID NO: 12
>Synthetic nucleotide primer or probe
AGCTGTAGAGAGGCCTGCCTCCA

>SEQ ID NO: 13
>Synthetic nucleotide primer or probe
TATCTTTGATTCTCCTTCAGCCCTCAC

---

What is claimed is:

1. A method for detecting an in-frame deletion mutation in exon 9 of the calreticulin (CALR) gene comprising:
   performing a nucleic acid detection assay on a patient sample to detect a CALR exon 9 in-frame deletion mutation, wherein the mutation is p.E381 _A382>A, characterized by a deletion of nucleotides 1142-1144 of SEQ ID NO: 1,
   wherein the patient sample is from a patient that has a myeloproliferative disease or is suspected of having a myeloproliferative disease, wherein the patient is negative for a JAK2 V617F mutation, and
   wherein the nucleic acid detection assay comprises using a primer pair comprising a forward primer of SEQ ID NO: 10 or 12 and/or a reverse primer of SEQ ID NO: 11 or 13.

2. The method of claim 1, wherein the method comprises nucleic acid amplification.

3. The method of claim 1, wherein the method comprises nucleic acid amplification using the primer pair.

4. The method of claim 1, wherein the method comprises polymerase chain reaction (PCR), reverse transcription polymerase chain reaction (RT-PCR), real-time PCR (qPCR), or nested PCR.

5. The method of claim 1, wherein the method comprises sequencing an amplicon comprising all or a portion of CALR exon 9 comprising the deletion.

6. The method of claim 5, wherein the amplicon is detected using a labeled oligonucleotide probe.

7. The method of claim 1, wherein the nucleic acid is DNA, cDNA, genomic DNA, or RNA.

8. The method of claim 1, wherein the patient sample is a blood, serum, plasma, or biopsy sample.

9. The method of claim 1, wherein the myeloproliferative disease is selected from among polycythemia vera, essential thrombocythemia, idiopathic myelofibrosis, and unclassified myeloproliferative disease.

10. The method of claim 1, further comprising detecting one or more additional mutations in one or more additional genes associated with a myeloproliferative disease, wherein the one or more additional genes is a JAK-STAT pathway gene.

11. The method of claim 10, wherein the one or more additional genes is JAK2, MPL, CSFR3R, ASXL1, or ZRSR2.

12. The method of claim 10, wherein the one or more additional mutations is selected from among a mutation in exon 12 or exon 14 of JAK2, exon 10 of MPL or exon 14 or exon 17 CSFR3R.

13. The method of claim 10, wherein the one or more additional mutations is selected from among MPL W515L, CSFR3R A470T, ASXL1 D954fs*26, and ZRSR2 S449_R450du.

14. The method of claim 1, further comprising using a labeled oligonucleotide probe to detect the in-frame deletion mutation, wherein the labeled oligonucleotide probe comprises from about 10 to 30 consecutive nucleotides of the sequence SEQ ID NO: 1 having a deletion of nucleotides 1142-1144 and overlaps the deletion site.

* * * * *

SEQUENCE LISTING

<160> NUMBER OF SEQ ID NOS: 32

<210> SEQ ID NO 1
<211> LENGTH: 1251
<212> TYPE: DNA
<213> ORGANISM: Homo sapiens

<400> SEQUENCE: 1

```
atgctgctat ccgtgccgct gctgctcggc ctcctcggcc tggccgtcgc cgagcctgcc      60
gtctacttca aggagcagtt tctggacgga gacgggtgga cttcccgctg gatcgaatcc     120
aaacacaagt cagattttgg caaattcgtt ctcagttccg gcaagttcta cggtgacgag     180
gagaaagata aggtttgca  gacaagccag gatgcacgct tttatgctct gtcggccagt     240
ttcgagcctt tcagcaacaa aggccagacg ctggtggtgc agttcacggt gaaacatgag     300
cagaacatcg actgtggggg cggctatgtg aagctgtttc ctaatagttt ggaccagaca     360
gacatgcacg gagactcaga atacaacatc atgtttggtc ccgacatctg tggccctggc     420
accaagaagg ttcatgtcat cttcaactac aagggcaaga acgtgctgat caacaaggac     480
atccgttgca aggatgatga gtttacacac tgtacacac tgattgtgcg ccagacaac      540 acctatgagg tgaagattga acagccag gtggagtccg gctccttgga agacgattgg     600
gacttcctgc cacccaagaa gataaaggat cctgatgctt caaaccgga agactgggat     660 gagcgggcca agatcgatga tcccacagac tccaagcctg aggactggga caagcccgag     720
catatccctg accctgatgc taagaagccc gaggactggg atgaagagat ggacggagag     780
tgggaacccc cagtgattca gaaccctgag tacaaaggtg agtggaagcc ccggcagatc     840
gacaacccag attacaaggg cacttggatc cacccagaaa ttgacaaccc cgagtattct     900
cccgatccca tatctatgc ctatgataac tttggcgtgc tgggcctgga cctctggcag     960
gtcaagtctg gcaccatctt tgacaacttc ctcatcacca cgatgaggc atacgctgag    1020 gagtttggca acgagacgtg gggcgtaaca aaggcagcag agaaacaaat gaaggacaaa    1080
```

```
caggacgagg agcagaggct taaggaggag gaagaagaca agaaacgcaa agaggaggag    1140
gaggcagagg acaaggagga tgatgaggac aaagatgagg atgaggagga tgaggaggac    1200
aaggaggaag atgaggagga agatgtcccc ggccaggcca aggacgagct g             1251
```

<210> SEQ ID NO 2
<211> LENGTH: 417
<212> TYPE: PRT
<213> ORGANISM: Homo sapiens

<400> SEQUENCE: 2

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
                35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
                115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
                195                 200                 205

Lys Asp Pro Asp Ala Ser Lys Pro Glu Asp Trp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
                260                 265                 270

Gly Glu Trp Lys Pro Arg Gln Ile Asp Asn Pro Asp Tyr Lys Gly Thr
                275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
```

```
                340                 345                 350
Ala Glu Lys Gln Met Lys Asp Lys Gln Asp Glu Glu Gln Arg Leu Lys
            355                 360                 365

Glu Glu Glu Glu Asp Lys Lys Arg Lys Glu Glu Glu Glu Ala Glu Asp
        370                 375                 380

Lys Glu Asp Asp Glu Asp Lys Asp Glu Asp Glu Asp Glu Glu Glu Asp
385                 390                 395                 400

Lys Glu Glu Asp Glu Glu Glu Asp Val Pro Gly Gln Ala Lys Asp Glu
                405                 410                 415

Leu

<210> SEQ ID NO 3
<211> LENGTH: 1929
<212> TYPE: DNA
<213> ORGANISM: Homo sapiens

<400> SEQUENCE: 3
```

| | | | | | |
|---|---|---|---|---|---|
| gcggcgtccg | tccgtactgc | agagccgctg | ccggagggtc | gttttaaagg | gcccgcgcgt | 60
| tgccgccccc | tcggcccgcc | atgctgctat | ccgtgccgct | gctgctcggc | ctcctcggcc | 120
| tggccgtcgc | cgagcctgcc | gtctacttca | aggagcagtt | tctggacgga | gacgggtgga | 180
| cttcccgctg | gatcgaatcc | aaacacaagt | cagattttgg | caaattcgtt | ctcagttccg | 240
| gcaagttcta | cggtgacgag | gagaaagata | aggtttgca | gacaagccag | gatgcacgct | 300
| tttatgctct | gtcggccagt | ttcgagcctt | tcagcaacaa | aggccagacg | ctggtggtgc | 360
| agttcacggt | gaaacatgag | cagaaacatcg | actgtggggg | cggctatgtg | aagctgtttc | 420
| ctaatagttt | ggaccagaca | gacatgcacg | gagactcaga | atacaacatc | atgtttggtc | 480
| ccgacatctg | tggccctggc | accaagaagg | ttcatgtcat | cttcaactac | aagggcaaga | 540
| acgtgctgat | caacaaggac | atccgttgca | aggatgatga | gtttacacac | ctgtacacac | 600
| tgattgtgcg | gccagacaac | acctatgagg | tgaagattga | caacagccag | gtggagtccg | 660
| gctccttgga | agacgattgg | gacttcctgc | cacccaagaa | gataaaggat | cctgatgctt | 720
| caaaaccgga | agactgggat | gagcgggcca | gatcgatga | tcccacagac | tccaagcctg | 780
| aggactggga | caagcccgag | catatccctg | accctgatgc | taagaagccc | gaggactggg | 840
| atgaagagat | ggacggagag | tgggaacccc | cagtgattca | gaaccctgag | tacaaggtg | 900
| agtggaagcc | ccggcagatc | gacaacccag | attacaaggg | cacttggatc | cacccagaaa | 960
| ttgacaaccc | cgagtattct | cccgatccca | gtatctatgc | ctatgataac | tttggcgtgc | 1020
| tgggcctgga | cctctggcag | gtcaagtctg | gcaccatctt | tgacaacttc | ctcatcacca | 1080
| acgatgaggc | atacgctgag | gagtttggca | acgagacgtg | gggcgtaaca | aaggcagcag | 1140
| agaaacaaat | gaaggacaaa | caggacgagg | agcagaggct | taaggaggag | gaagaagaca | 1200
| agaaacgcaa | agaggaggag | gaggcagagg | acaaggagga | tgatgaggac | aaagatgagg | 1260
| atgaggagga | tgaggaggac | aaggaggaag | atgaggagga | agatgtcccc | ggccaggcca | 1320
| aggacgagct | gtagagaggc | ctgcctccag | ggctggactg | aggcctgagc | gctcctgccg | 1380
| cagagctggc | cgcgccaaat | aatgtctctg | tgagactcga | gaactttcat | tttttttccag | 1440
| gctggttcgg | atttggggtg | gattttggtt | ttgttcccct | cctccactct | cccccacccc | 1500
| ctccccgccc | tttttttttt | tttttttaa | actggtattt | tatctttgat | tctccttcag | 1560
| ccctcacccc | tggttctcat | cttcttgat | caacatcttt | tcttgcctct | gtcccttct | 1620
| ctcatctctt | agctcccctc | caacctgggg | ggcagtggtg | tggagaagcc | acaggcctga | 1680

-continued

```
gatttcatct gctctccttc ctggagccca gaggagggca gcagaagggg gtggtgtctc    1740
caacccccca gcactgagga agaacggggc tcttctcatt tcaccccctcc ctttctcccc    1800 tgccccccagg actgggccac ttctgggtgg ggcagtgggt cccagattgg ctcacactga    1860
gaatgtaaga actacaaaca aaatttctat taaattaaat tttgtgtctc caaaaaaaaa    1920
aaaaaaaaa                                                              1929
```

<210> SEQ ID NO 4
<211> LENGTH: 414
<212> TYPE: PRT
<213> ORGANISM: Pan troglodytes

<400> SEQUENCE: 4

```
Met Leu Leu Ser Val Pro Leu Leu Gly Leu Leu Gly Leu Ala Val
1               5                   10                  15

Ala Glu Pro Ala Val Tyr Phe Lys Glu Gln Phe Leu Asp Gly Asp
                20                  25                  30

Trp Thr Ser Arg Trp Ile Glu Ser Lys His Lys Ser Asp Phe Gly Lys
                35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asn Ser Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
            130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Pro Ser
    290                 295                 300

Ile Tyr Ala Tyr Asp Asn Phe Gly Val Leu Gly Leu Asp Leu Trp Gln
305                 310                 315                 320
```

-continued

```
Val Lys Ser Gly Thr Ile Phe Asp Asn Phe Leu Ile Thr Asn Asp Glu
            325                 330                 335

Ala Tyr Ala Glu Glu Phe Gly Asn Glu Thr Trp Gly Val Thr Lys Ala
        340                 345                 350

Ala Glu Lys Gln Met Lys Asp Lys Gln Asp Glu Glu Gln Arg Leu Lys
    355                 360                 365

Glu Glu Glu Glu Asp Lys Lys Arg Lys Glu Glu Glu Ala Glu Asp
370                 375                 380

Lys Glu Asp Asp Glu Asp Lys Asp Glu Asp Glu Asp Lys Glu Glu
385                 390                 395                 400

Asp Glu Glu Glu Asp Val Pro Gly Gln Ala Lys Asp Glu Leu
            405                 410
```

<210> SEQ ID NO 5
<211> LENGTH: 417
<212> TYPE: PRT
<213> ORGANISM: Macaca mulatta

<400> SEQUENCE: 5

```
Met Leu Leu Ser Val Pro Leu Leu Gly Leu Leu Gly Leu Ala Ala
1               5                   10                  15

Ala Glu Pro Ala Val Tyr Phe Lys Glu Gln Phe Leu Asp Gly Asp Gly
            20                  25                  30

Trp Thr Ser Arg Trp Ile Glu Ser Lys His Lys Ser Asp Phe Gly Lys
        35                  40                  45

Phe Val Leu Ser Ser Gly Lys Phe Tyr Gly Asp Glu Glu Lys Asp Lys
    50                  55                  60

Gly Leu Gln Thr Ser Gln Asp Ala Arg Phe Tyr Ala Leu Ser Ala Ser
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Asn Ser Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285
```

Trp Ile His Pro Glu Ile Asp Asn Pro Glu Tyr Ser Pro Asp Pro Ser
            290                 295                 300

Ile Tyr Ala Tyr Asp Asn Phe Gly Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
            370                 375                 380

Lys Glu Asp Asp Glu Asp Lys Asp Glu Asp Glu Asp Glu Asp
385                 390                 395                 400

Lys Glu Glu Asp Glu Glu Asp Val Pro Gly Gln Ala Lys Asp Glu
                405                 410                 415

Leu

<210> SEQ ID NO 6
<211> LENGTH: 417
<212> TYPE: PRT
<213> ORGANISM: Canis lupus familiaris

<400> SEQUENCE: 6

Met Leu Leu Pro Val Pro Leu Leu Gly Leu Val Gly Leu Ala Ala
1               5                   10                  15

Ala Glu Pro Ala Ile Tyr Phe Lys Glu Gln Phe Leu Asp Gly Asp
            20                  25                  30

Trp Thr Asp Arg Trp Ile Glu Ser Lys His Lys Ser Asp Phe Gly Lys
            35                  40                  45

Phe Val Leu Ser Ser Gly Lys Phe Tyr Asn Asp Gln Glu Lys Asp Lys
50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
                100                 105                 110

Phe Pro Asp Gly Leu Asp Gln Thr Asp Met His Gly Asp Ser Glu Tyr
            115                 120                 125

Asn Ile Met Phe Gly Pro Asp Ile Cys Gly Pro Gly Thr Lys Lys Val
130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ser Lys Pro Glu Asp Trp Asp Glu Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
            245                 250                 255

Met Asp Gly Glu Trp Glu Pro Pro Val Ile Gln Asn Pro Glu Tyr Lys
        260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Ser Asn
    290                 295                 300

Ile Tyr Ala Tyr Glu Asn Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Glu Ala Asp Lys
    370                 375                 380

Glu Asp Glu Glu Asp Lys Asp Glu Asp Glu Glu Asp Glu Asp Asp Lys
385                 390                 395                 400

Glu Glu Glu Glu Glu Asp Asp Ala Ala Ala Gly Gln Ala Lys Asp Glu
                405                 410                 415

Leu

<210> SEQ ID NO 7
<211> LENGTH: 417
<212> TYPE: PRT
<213> ORGANISM: Bos taurus

<400> SEQUENCE: 7

Met Leu Leu Pro Val Pro Leu Leu Gly Leu Leu Gly Leu Ala Ala
1               5                   10                  15

Ala Asp Pro Thr Val Tyr Phe Lys Glu Gln Phe Leu Asp Gly Asp Gly
            20                  25                  30

Trp Thr Glu Arg Trp Ile Glu Ser Lys His Lys Pro Asp Phe Gly Lys
        35                  40                  45

Phe Val Leu Ser Ser Gly Lys Phe Tyr Gly Asp Gln Glu Lys Asp Lys
    50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Ala Gly Leu Asp Gln Thr Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asn Asn Thr Tyr Glu Val Lys Ile Asp Asn Ser Gln Val Glu
            180                 185                 190

```
Ser Gly Ser Leu Glu Asp Asp Trp Asp Phe Leu Pro Pro Lys Lys Ile
        195                 200                 205

Lys Asp Pro Asp Ala Ala Lys Pro Glu Asp Trp Asp Arg Ala Lys
210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
        260                 265                 270

Gly Glu Trp Lys Pro Arg Gln Ile Asp Asn Pro Glu Tyr Lys Gly Ile
        275                 280                 285

Trp Ile His Pro Glu Ile Asp Asn Pro Glu Tyr Ser Pro Asp Ser Asn
290                 295                 300

Ile Tyr Ala Tyr Glu Asn Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
        340                 345                 350

Ala Glu Lys Gln Met Lys Asp Lys Gln Asp Glu Glu Gln Arg Leu His
        355                 360                 365

Glu Glu Glu Glu Glu Lys Lys Gly Lys Glu Glu Glu Ala Asp Lys
370                 375                 380

Asp Asp Asp Glu Asp Lys Asp Glu Asp Glu Asp Glu Asp Glu Lys
385                 390                 395                 400

Glu Glu Glu Glu Glu Glu Asp Ala Ala Ala Gly Gln Ala Lys Asp Glu
                405                 410                 415

Leu

<210> SEQ ID NO 8
<211> LENGTH: 416
<212> TYPE: PRT
<213> ORGANISM: Mus musculus

<400> SEQUENCE: 8

Met Leu Leu Ser Val Pro Leu Leu Leu Gly Leu Leu Gly Leu Ala Ala
1               5                   10                  15

Ala Asp Pro Ala Ile Tyr Phe Lys Glu Gln Phe Leu Asp Gly Asp Ala
            20                  25                  30

Trp Thr Asn Arg Trp Val Glu Ser Lys His Lys Ser Asp Phe Gly Lys
        35                  40                  45

Phe Val Leu Ser Ser Gly Lys Phe Tyr Gly Asp Leu Glu Lys Asp Lys
    50                  55                  60

Gly Leu Gln Thr Ser Gln Asp Ala Arg Phe Tyr Ala Leu Ser Ala Lys
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu
            100                 105                 110

Phe Pro Ser Gly Leu Asp Gln Lys Asp Met His Gly Asp Ser Glu Tyr
        115                 120                 125

Asn Ile Met Phe Gly Pro Asp Ile Cys Gly Pro Gly Thr Lys Lys Val
    130                 135                 140
```

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
            180                 185                 190

Ser Gly Ser Leu Glu Asp Asp Trp Asp Phe Leu Pro Pro Lys Lys Ile
        195                 200                 205

Lys Asp Pro Asp Ala Ala Lys Pro Glu Asp Trp Asp Glu Arg Ala Lys
    210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
        275                 280                 285

Trp Ile His Pro Glu Ile Asp Asn Pro Glu Tyr Ser Pro Asp Ala Asn
290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Ala
            340                 345                 350

Ala Glu Lys Gln Met Lys Asp Lys Gln Asp Glu Glu Gln Arg Leu Lys
        355                 360                 365

Glu Glu Glu Glu Asp Lys Lys Arg Lys Glu Glu Glu Ala Glu Asp
    370                 375                 380

Lys Glu Asp Asp Asp Asp Arg Asp Glu Asp Glu Asp Glu Glu Asp Glu
385                 390                 395                 400

Lys Glu Glu Asp Glu Glu Glu Ser Pro Gly Gln Ala Lys Asp Glu Leu
                405                 410                 415

<210> SEQ ID NO 9
<211> LENGTH: 416
<212> TYPE: PRT
<213> ORGANISM: Rattus norvegicus

<400> SEQUENCE: 9

Met Leu Leu Ser Val Pro Leu Leu Leu Gly Leu Leu Gly Leu Ala Ala
1               5                   10                  15

Ala Asp Pro Ala Ile Tyr Phe Lys Glu Gln Phe Leu Asp Gly Asp Ala
            20                  25                  30

Trp Thr Asn Arg Trp Val Glu Ser Lys His Lys Ser Asp Phe Gly Lys
        35                  40                  45

Phe Val Leu Ser Ser Gly Lys Phe Tyr Gly Asp Gln Glu Lys Asp Lys
    50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Thr Leu Val Val Gln Phe Thr
                85                  90                  95

Val Lys His Glu Gln Asn Ile Asp Cys Gly Gly Gly Tyr Val Lys Leu

```
            100                 105                  110
Phe Pro Gly Gly Leu Asp Gln Lys Asp Met His Gly Asp Ser Glu Tyr
            115                  120             125

Asn Ile Met Phe Gly Pro Asp Ile Cys Gly Pro Gly Thr Lys Lys Val
        130                 135             140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170             175

Arg Pro Asp Asn Thr Tyr Glu Val Lys Ile Asp Asn Ser Gln Val Glu
            180                 185             190

Ser Gly Ser Leu Glu Asp Asp Trp Asp Phe Leu Pro Pro Lys Lys Ile
        195                 200             205

Lys Asp Pro Asp Ala Ala Lys Pro Glu Asp Trp Asp Glu Arg Ala Lys
210             215                 220

Ile Asp Asp Pro Thr Asp Ser Lys Pro Glu Asp Trp Asp Lys Pro Glu
225             230             235                 240

His Ile Pro Asp Pro Asp Ala Lys Lys Pro Glu Asp Trp Asp Glu Glu
                245             250             255

Met Asp Gly Glu Trp Glu Pro Pro Val Ile Gln Asn Pro Glu Tyr Lys
            260             265             270

Gly Glu Trp Lys Pro Arg Gln Ile Asp Asn Pro Asp Tyr Lys Gly Thr
        275             280             285

Trp Ile His Pro Glu Ile Asp Asn Pro Glu Tyr Ser Pro Asp Ala Asn
    290             295             300

Ile Tyr Ala Tyr Asp Ser Phe Ala Val Leu Gly Leu Asp Leu Trp Gln
305             310             315             320

Val Lys Ser Gly Thr Ile Phe Asp Asn Phe Leu Ile Thr Asn Asp Glu
            325             330             335

Ala Tyr Ala Glu Glu Phe Gly Asn Glu Thr Trp Gly Val Thr Lys Ala
        340             345             350

Ala Glu Lys Gln Met Lys Asp Lys Gln Asp Glu Glu Gln Arg Leu Lys
        355             360             365

Glu Glu Glu Glu Asp Lys Lys Arg Lys Glu Glu Glu Glu Ala Glu Asp
    370             375             380

Lys Glu Asp Glu Asp Asp Arg Asp Glu Asp Glu Asp Glu Glu Asp Glu
385             390             395             400

Lys Glu Glu Asp Glu Glu Asp Ala Thr Gly Gln Ala Lys Asp Glu Leu
            405             410             415
```

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggagcgctc aggcctcagt ccagcc                                          26

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
caggcagagc acacacctca gg                                            22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agctgtagag aggcctgcct cca                                           23

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tatctttgat tctccttcag ccctcac                                       27

<210> SEQ ID NO 14
<211> LENGTH: 4
<212> TYPE: PRT
<213> ORGANISM: Unknown
<220> FEATURE:
<223> OTHER INFORMATION: Description of Unknown:
      Wild-type ER-retention motif

<400> SEQUENCE: 14

Lys Asp Glu Leu
1

<210> SEQ ID NO 15
<211> LENGTH: 4
<212> TYPE: PRT
<213> ORGANISM: Homo sapiens

<400> SEQUENCE: 15

Asp Glu Glu Asp
1

<210> SEQ ID NO 16
<211> LENGTH: 12
<212> TYPE: DNA
<213> ORGANISM: Homo sapiens

<400> SEQUENCE: 16
aggaggaaga tg                                                       12

<210> SEQ ID NO 17
<211> LENGTH: 5
<212> TYPE: PRT
<213> ORGANISM: Homo sapiens

<400> SEQUENCE: 17

Glu Glu Glu Asp Val
1               5

-continued

```
<210> SEQ ID NO 18
<211> LENGTH: 22
<212> TYPE: DNA
<213> ORGANISM: Unknown
<220> FEATURE:
<223> OTHER INFORMATION: Description of Unknown:
      Wild-type CALR sequence

<400> SEQUENCE: 18
gaggatgagg aggacaagga gg                                            22

<210> SEQ ID NO 19
<211> LENGTH: 8
<212> TYPE: PRT
<213> ORGANISM: Unknown
<220> FEATURE:
<223> OTHER INFORMATION: Description of Unknown:
      Wild-type CALR sequence

<400> SEQUENCE: 19

Glu Asp Glu Glu Asp Lys Glu Glu
1               5

<210> SEQ ID NO 20
<211> LENGTH: 13
<212> TYPE: DNA
<213> ORGANISM: Unknown
<220> FEATURE:
<223> OTHER INFORMATION: Description of Unknown:
      Wild-type CALR sequence

<400> SEQUENCE: 20
gaggacaagg agg                                                      13

<210> SEQ ID NO 21
<211> LENGTH: 29
<212> TYPE: PRT
<213> ORGANISM: Homo sapiens

<400> SEQUENCE: 21

Glu Ala Glu Asp Lys Glu Asp Asp Glu Asp Lys Asp Glu Asp Glu Glu
1               5                   10                  15

Asp Glu Glu Asp Lys Glu Glu Asp Glu Glu Glu Asp Val
            20                  25

<210> SEQ ID NO 22
<211> LENGTH: 26
<212> TYPE: PRT
<213> ORGANISM: Pan troglodytes

<400> SEQUENCE: 22

Glu Ala Glu Asp Lys Glu Asp Asp Glu Asp Lys Asp Glu Asp Glu Glu
1               5                   10                  15

Asp Lys Glu Glu Asp Glu Glu Glu Asp Val
            20                  25

<210> SEQ ID NO 23
<211> LENGTH: 29
<212> TYPE: PRT
<213> ORGANISM: Macaca mulatta

<400> SEQUENCE: 23

Glu Ala Glu Asp Lys Glu Asp Asp Glu Asp Lys Asp Glu Asp Glu Glu
1               5                   10                  15

Asp Glu Glu Asp Lys Glu Glu Asp Glu Glu Glu Asp Val
```

<210> SEQ ID NO 24
<211> LENGTH: 29
<212> TYPE: PRT
<213> ORGANISM: Canis lupus familiaris

<400> SEQUENCE: 24

Glu Ala Asp Lys Glu Asp Glu Asp Lys Asp Glu Asp Glu Asp
1               5                   10                  15

Glu Asp Asp Lys Glu Glu Glu Glu Asp Asp Ala Ala
            20                  25

<210> SEQ ID NO 25
<211> LENGTH: 28
<212> TYPE: PRT
<213> ORGANISM: Mus musculus

<400> SEQUENCE: 25

Glu Ala Glu Asp Lys Glu Asp Asp Asp Arg Asp Glu Asp Glu Asp
1               5                   10                  15

Glu Glu Asp Glu Lys Glu Glu Asp Glu Glu Glu Ser
            20                  25

<210> SEQ ID NO 26
<211> LENGTH: 28
<212> TYPE: PRT
<213> ORGANISM: Rattus norvegicus

<400> SEQUENCE: 26

Glu Ala Glu Asp Lys Glu Asp Glu Asp Asp Arg Asp Glu Asp Glu Asp
1               5                   10                  15

Glu Glu Asp Glu Lys Glu Glu Asp Glu Glu Asp Ala
            20                  25

<210> SEQ ID NO 27
<211> LENGTH: 22
<212> TYPE: DNA
<213> ORGANISM: Unknown
<220> FEATURE:
<223> OTHER INFORMATION: Description of Unknown:
      Wild-type CALR sequence

<400> SEQUENCE: 27
gatgaggagg aagatgtccc cg                                              22

<210> SEQ ID NO 28
<211> LENGTH: 8
<212> TYPE: PRT
<213> ORGANISM: Unknown
<220> FEATURE:
<223> OTHER INFORMATION: Description of Unknown:
      Wild-type CALR sequence

<400> SEQUENCE: 28

Asp Glu Glu Glu Asp Val Pro Gly
1               5

<210> SEQ ID NO 29
<211> LENGTH: 10
<212> TYPE: DNA
<213> ORGANISM: Unknown
<220> FEATURE:
<223> OTHER INFORMATION: Description of Unknown:
      Wild-type CALR sequence

```
<400> SEQUENCE: 29
gatgtccccg                                                              10

<210> SEQ ID NO 30
<211> LENGTH: 22
<212> TYPE: DNA
<213> ORGANISM: Unknown
<220> FEATURE:
<223> OTHER INFORMATION: Description of Unknown:
      Wild-type CALR sequence

<400> SEQUENCE: 30
gaggaggagg cagaggacaa gg                                                22

<210> SEQ ID NO 31
<211> LENGTH: 8
<212> TYPE: PRT
<213> ORGANISM: Unknown
<220> FEATURE:
<223> OTHER INFORMATION: Description of Unknown:
      Wild-type CALR sequence

<400> SEQUENCE: 31

Glu Glu Glu Ala Glu Asp Lys Glu
1               5

<210> SEQ ID NO 32
<211> LENGTH: 19
<212> TYPE: DNA
<213> ORGANISM: Unknown
<220> FEATURE:
<223> OTHER INFORMATION: Description of Unknown:
      Wild-type CALR sequence

<400> SEQUENCE: 32
gaggaggcag aggacaagg                                                    19
```